(12) United States Patent
Szalecki et al.

(10) Patent No.: US 6,562,632 B1
(45) Date of Patent: May 13, 2003

(54) REACTIVE DERIVATIVES OF SULFORHODAMINE 101 WITH ENHANCED HYDROLYTIC STABILITY

(75) Inventors: Wojciech Szalecki, Eugene, OR (US); Richard P. Haugland, Eugene, OR (US)

(73) Assignee: Molecular Probes, Inc., Eugene, OR (US)

( * ) Notice: Subject to any disclaimer, the term of this patent is extended or adjusted under 35 U.S.C. 154(b) by 345 days.

(21) Appl. No.: 09/129,015

(22) Filed: Aug. 4, 1998

Related U.S. Application Data

(62) Division of application No. 08/485,033, filed on Jun. 7, 1995, now Pat. No. 5,798,276.

(51) Int. Cl.[7] .................... G01N 33/533; C07D 221/22
(52) U.S. Cl. .................. 436/546; 436/800; 546/37
(58) Field of Search .................. 546/37, 546, 800

(56) References Cited

U.S. PATENT DOCUMENTS

| | | | |
|---|---|---|---|
| 4,711,955 A | 12/1987 | Ward et al. .................. 536/29 |
| 5,047,519 A | 9/1991 | Hobbs, Jr. et al. ............ 536/27 |
| 5,175,269 A | 12/1992 | Stavrianopoulos ........... 536/27 |
| 5,241,060 A | 8/1993 | Englehardt et al. ........... 536/27 |
| 5,328,824 A | 7/1994 | Ward et al. .................. 436/7.1 |
| 5,362,628 A | 11/1994 | Haugland et al. ............. 435/18 |
| 5,393,514 A | 2/1995 | Pitner et al. ................. 424/7.1 |
| 5,512,486 A | 4/1996 | Giese et al. .................. 436/63 |
| 5,576,424 A | 11/1996 | Haugland et al. ........... 536/17.9 |
| 5,650,512 A | 7/1997 | Ahlem et al. ................ 546/37 |
| 5,798,276 A | 8/1998 | Haugland et al. ........... 436/546 |
| 5,955,612 A * | 9/1999 | Ahlem et al. ................ 546/37 |

FOREIGN PATENT DOCUMENTS

EP         0 229 943         9/1991

OTHER PUBLICATIONS

Titus, et al., J. Immunol. Meth., 50, 193 (1982).
Waggoner, et al., Principles of Clinical Flow Cytometry, Chapter 7, pp. 111–116.
Abuelyaman, et al. Bioconjugate Chem., 5, 400 (1994).
Haugland, Molecular Probes Handbook of Fluorescent Probes and Research Chemicals (1992) (Table of Contents Only).
Wittung, et al., Nature 368, 561 (1994).
Brinkley, et al., Bioconjugate Chem., 3, 2 (1992).
Amlaiky, et al., FEBS Lett. 176, 436 (1984).
Johnson et al. Biochemistry, 33, 9070 (1994).
Marchesini et al. Chem. Phys. Lipids 72, 143 (1994).
TEXAS RED® and its Protein Conjugates, Product Information Sheet, Molecular Probes, Inc.
Chromatidesô—Labeled Nucleoside Triphosphates, Product Information Sheet, Molecular Probes, Inc.
Lefevre et al. Bioconjugate Chemistry 7, 482 (1996).
Chem Abstracts 124:166619 (Wiemann et al. Anal. Biochem. 234, 166 (1996)).

* cited by examiner

*Primary Examiner*—Mary E. Ceperley
(74) *Attorney, Agent, or Firm*—Allegra Helfenstein; Anton Skaugset

(57) ABSTRACT

The invention describes reactive dyes having an alkyl spacer attached via a sulfonamide bond to a sulforhodamine 101 fluorophore, and a variety of useful conjugates prepared therefrom. The increased length of the covalent linkage due to the alkyl spacer results in dye-conjugates having a number of surprisingly advantageous properties relative to previous sulforhodamine 101-labeled conjugates, including enhanced solubility and increased fluorescence. The reactive dyes of the present invention are more stable than the known compound sulforhodamine 101 sulfonyl chloride. Novel reactive dyes are described for selective modification of groups other than amines, including thiols and photoreactive derivatives.

19 Claims, 6 Drawing Sheets

REACTIVE DERIVATIVES OF SULFORHODAMINE 101 WITH ENHANCED HYDROLYTIC STABILITY

This application is a division of application Ser. No. 08/485,033, filed Jun. 7, 1995, now U.S. Pat. No. 5,798,276.

FIELD OF THE INVENTION

The invention relates to a family of fluorescent labeled conjugates of sulforhodamine 101, and the chemically reactive fluorescent dyes that are used to prepare those conjugates, including a wide range of biologically-derived or synthetic chemical materials.

BACKGROUND

Fluorescent dyes are known to be particularly suitable for biological applications in which a highly sensitive detection reagent is desirable. Fluorescent dyes are used to impart both visible color and fluorescence to other materials. Dyes that are able to preferentially bind to a specific biological ingredient in a sample enable the researcher to determine the presence or quantity of that specific ingredient. In addition, specific cellular structures can be monitored with respect to their spatial and temporal distribution in diverse environments. Many applications utilize chemically reactive fluorescent dyes by chemically attaching the dye to reactive sites on a wide variety of materials such as cells, tissues, proteins, antibodies, enzymes, drugs, hormones, lipids, nucleotides, nucleic acids, or natural or synthetic polymers to make fluorescent conjugates.

Reactive derivatives of a wide variety of fluorescent dyes have been previously described. This family of reactive dyes includes the sulfonyl chloride derivative of sulforhodamine 101 (Titus et al. J. IMMUNOL. METH., 50, 193 (1982)), sold by Molecular Probes, Inc. under its registered trademark TEXAS RED. The sulfonyl chloride of sulforhodamine 101 (hereafter referred to as SSC) is typically available as a mixture of isomers, as shown below:

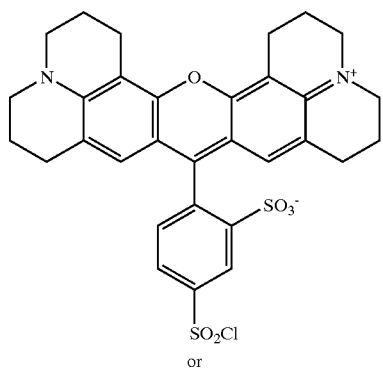

or

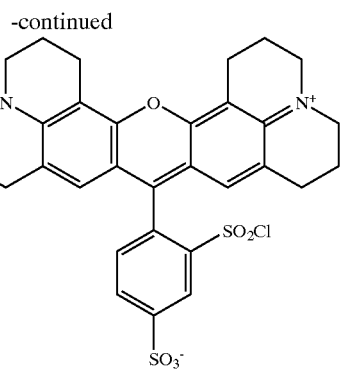

Conjugates of SSC with proteins and other biomolecules have achieved wide acceptance, particularly because their red fluorescence is readily distinguishable from that of fluorescein (FIG. 2), with which they are often combined in assays (Titus et al., supra).

Despite its many favorable characteristics, SSC possesses several disadvantages when used as a protein label. It is difficult to prepare protein conjugates that have a high degree of SSC-labeling due to the strong tendency of the resulting SSC-conjugates to precipitate from solution (Titus et al., supra; Waggoner et al., PRINCIPLES OF CLINICAL FLOW CYTOMETRY, Chapter 7, pp 111–116). Furthermore, SSC is not appreciably soluble in water, necessitating prior dissolution of SSC in an organic solvent, which must then be added to the protein. In addition, the short spacer between SSC and the attachment site makes SSC-conjugates more likely to hinder the labeled probe in biological interactions, such as with an enzyme, as when the SSC-labeled nucleotides are used in conjunction with a nucleotide polymerase, or with a ligand binding site, as in the case of a drug receptor. Finally, the fluorescence emission of SSC-labeled proteins tends to be quenched, relative to the fluorescence emission of the free dye.

In addition, the SSC dye itself possesses a sulfonyl chloride reactive site, so it is intrinsically very susceptible to hydrolysis by even trace amounts of water. This instability often results in labeling variability, or total labeling failure. Sulfonyl chlorides also react non-selectively with groups in proteins other than amines, including tyrosine, histidine and serine residues. Where these residues are essential for biological activity of the proteins, this reactivity is detrimental to the use of the labeled protein. Furthermore, instability of these undesired adducts results in slow loss of the dye from the conjugates during storage.

The modification of SSC to form the dyes of the present invention allows the use of other less problematic reactive groups on the fluorophore, allowing conjugation with a wider range of substances. Derivatives of sulforhodamine 101 that selectively react with functional groups other than amines (e.g. thiol-reactive dyes) were previously unknown. An aminocaproic acid derivative of sulforhodamine 101 has recently been described in the literature (Abuelyaman et al., BIOCONJUGATE CHEM. 5, 400 (1994)), used as the hydroxybenzotriazole ester to prepare only a particular sulforhodamine 101-labeled peptide phosphonate. The resulting intermediate activated ester is less chemically stable than analogous N-hydroxysuccinimidyl esters. Succinimidyl esters of aminoalkanoic acids are known for other fluorophores, including tetramethylrhodamine (Haugland, MOLECULAR PROBES HANDBOOK OF FLUORESCENT PROBES AND RESEARCH CHEMICALS, (1992)) and lissamine rhodamine (U.S. Pat. No. 5,393,514 to Pitner et al., (1995)). These fluorophores possess a shorter wavelength than those of the present invention, and they do not possess all of the advantages of the reactive dyes of the invention, in particular, a fluorescence emission that is well separated from that of fluorescein.

The novel dyes of the invention are derived from SSC, but they possess many advantages that overcome the cited limitations of SSC, including greater water solubility, selective reactivity with a broader range of functional groups, and considerably enhanced stability relative to SSC. The reactive dyes have sufficient chemical stability to permit their purification to a high degree of purity, including their separation into chemically pure single isomers, and the removal of trace amounts of disulfonyl chloride impurity, which is not practical for the hydrolytically unstable SSC. In addition, the conjugates that result from the use of the new dyes retain or improve upon the beneficial properties of labeling with sulforhodamine 101. Selected embodiments of the invention react with, and form conjugates with, substances having reactive functional groups, including amines, thiols, alcohols and phenols. The conjugates of the present invention have fluorescence emission wavelengths that are the same or longer in wavelength than those prepared from SSC, and thus have even less spectral overlap with the emission of fluorescein (FIG. 2). Furthermore, the conjugates prepared using the dyes of the present invention typically possess a higher fluorescence quantum yield than SSC-conjugates, both as the result of permitting a higher degree of substitution, and an unexpected reduction of quenching of the dyes by their conjugates (FIG. 7). The protein-conjugates of the present invention are unexpectedly much more soluble than those prepared using SSC, and are less prone to precipitation. Finally, the dyes of the present invention label oligonucleotides more efficiently than SSC, and the resulting oligonucleotide conjugates are more readily purified.

SUMMARY OF THE INVENTION AND DESCRIPTION OF PREFERRED EMBODIMENTS

Figure 1:
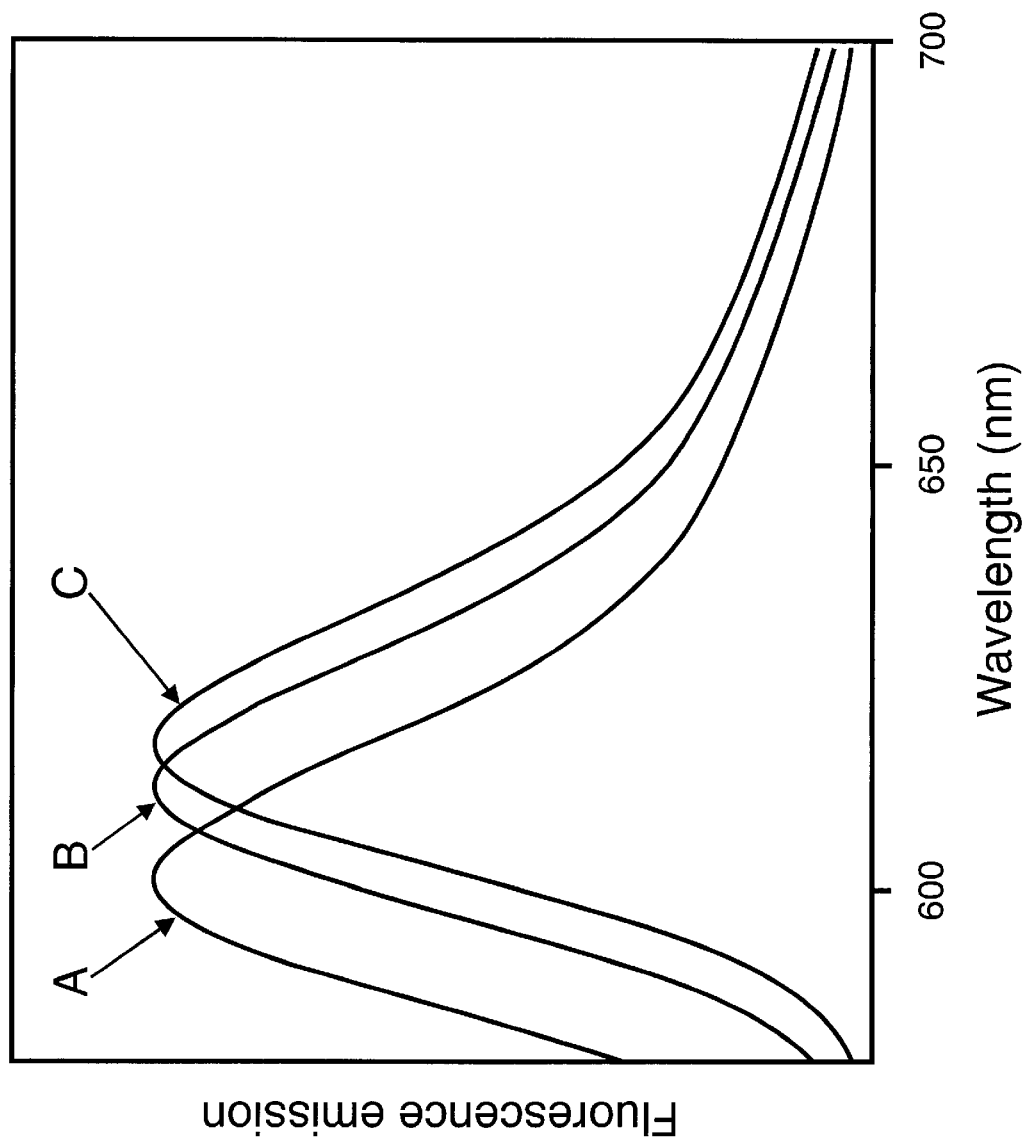
FIG. 1: The normalized fluorescence emission spectra of selected conjugates of streptavidin. A) rhodamine-x isothiocyanate, B) SSC-streptavidin and C) Compound 2-streptavidin conjugate (Example 19).
Figure 2:
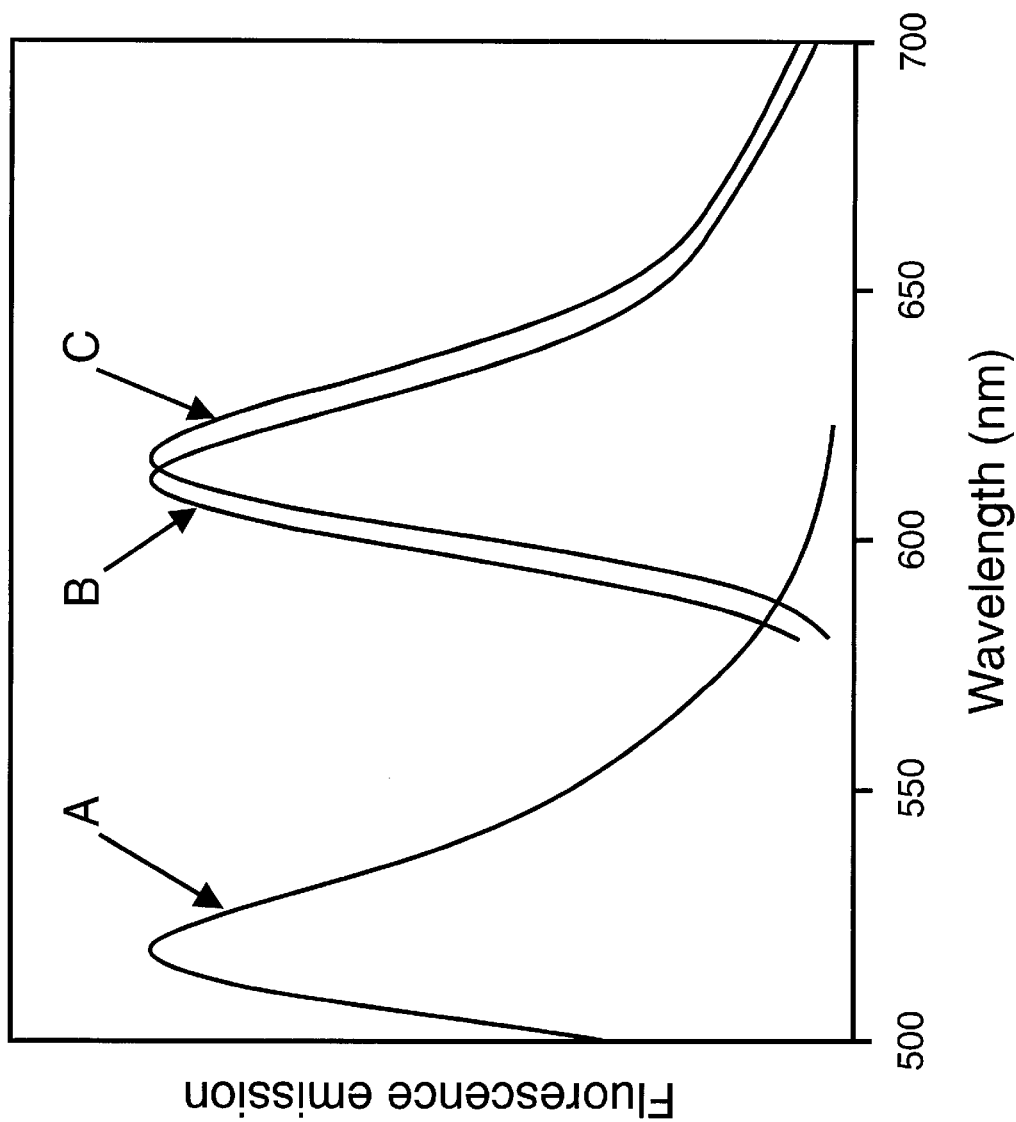
FIG. 2: The normalized fluorescence emission spectra of selected conjugates of goat IgG antibody. A) fluorescein, B) SSC, and C) Compound 2 (Example 19).
Figure 3:
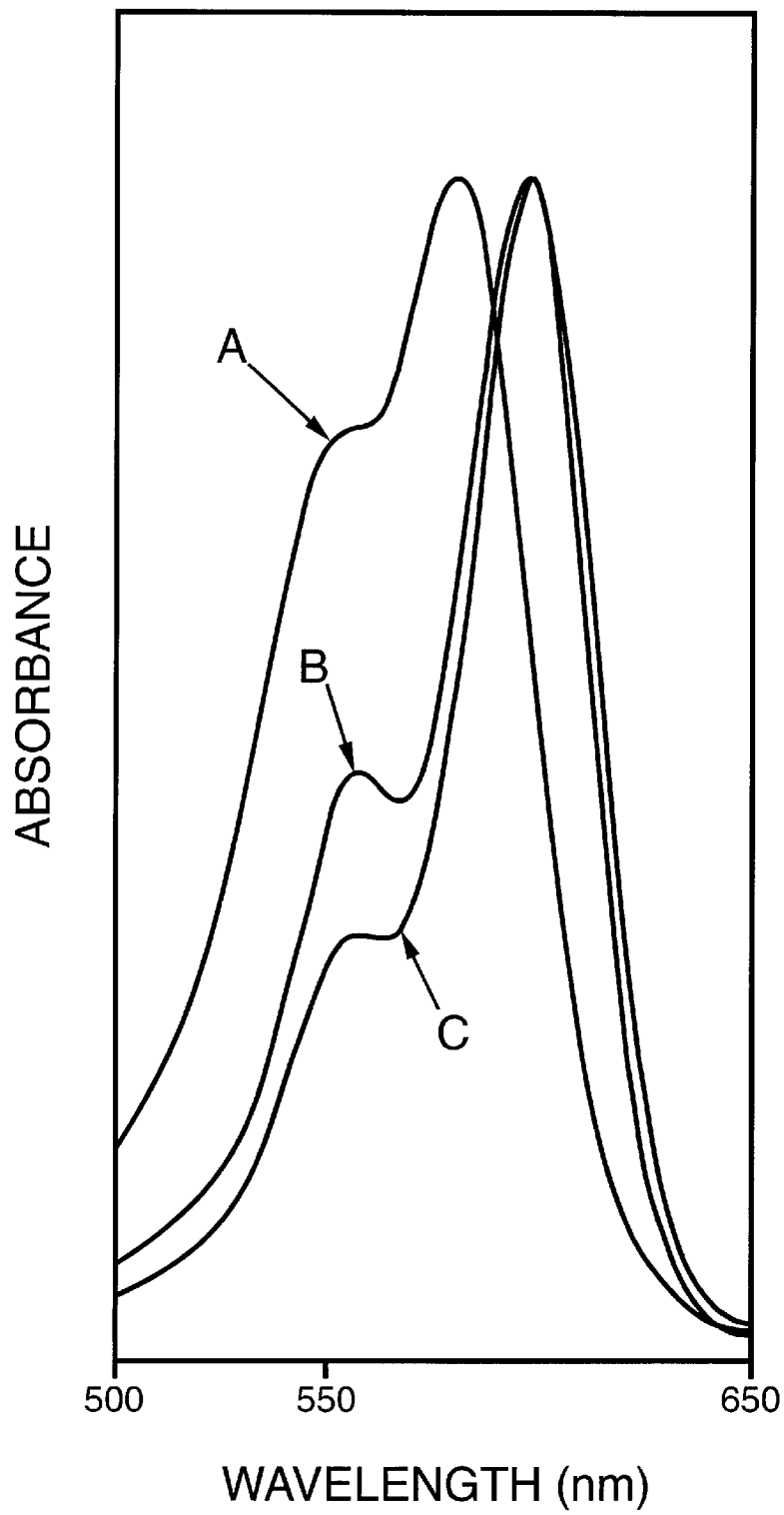
FIG. 3: The normalized absorption spectra of selected conjugates of streptavidin in PBS at pH 7.2: A) rhodamine-X isothiocyanate (XRITC), B) SSC, C) Compound 2.
Figure 4:
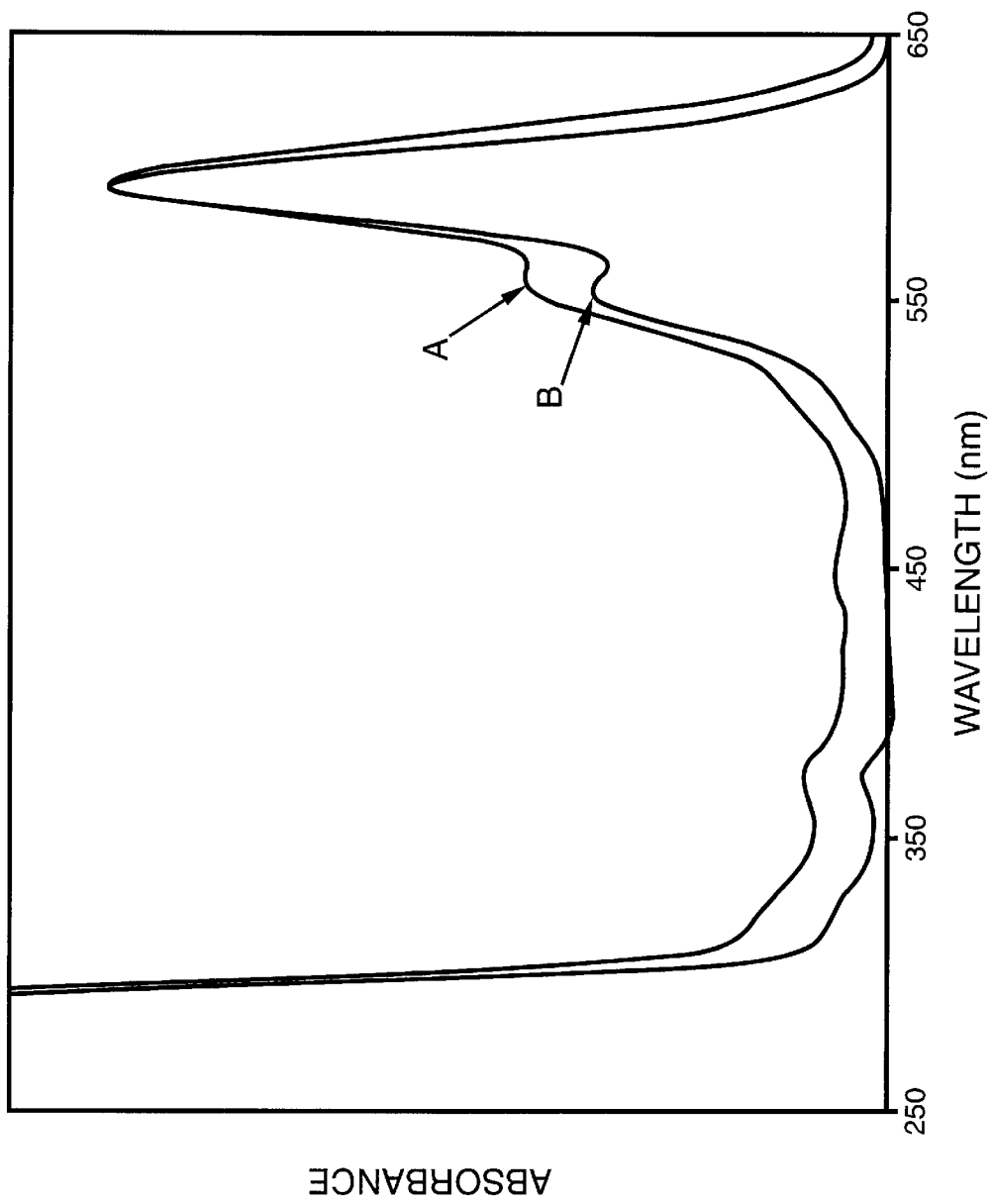
FIG. 4: The normalized absorption spectra of goat anti-mouse antibody conjugates of A) SSC, and B) Compound 2 (Example 19).

Reactive dyes of the invention have an alkyl spacer attached by a sulfonamide bond to a sulforhodamine 101 fluorophore. The increased length of the covalent linkage due to the alkyl spacer results in dye-conjugates having a number of surprisingly advantageous properties relative to previous sulforhodamine 101-labeled conjugates, including enhanced water solubility and increased fluorescence. The reactive dyes of the present invention are more stable than the known compound sulforhodamine 101 sulfonyl chloride ("SSC"). Novel reactive dyes are described for selective modification of amines, as well as other groups, including thiols and photoreactive derivatives.

Reactive Dyes

The reactive dyes of the present invention are all derivatives prepared from SSC. As with SSC, the reactive dyes of the invention are typically available as a mixture of the two mono-sulfonyl isomers of sulforhodamine 101, typically containing some disulfonyl derivative. While the parent material, SSC, is insufficiently stable to permit a practical separation of the isomers and contaminants, the reactive dyes of the present invention are typically stable enough for the isomers to be purified by conventional means, including column chromatography and high performance liquid chromatography (HPLC). While the two isomers are generally equivalent for many of the purposes of the present invention, purification of discrete isomers is sometimes required for the most critical assays. It is understood that while the "para" sulfonamide isomer is typically shown and referred to, unless specifically stated otherwise, each isomer as well as mixtures of both isomers are encompassed by the present invention.

The reactive dyes of the present invention have the general formula

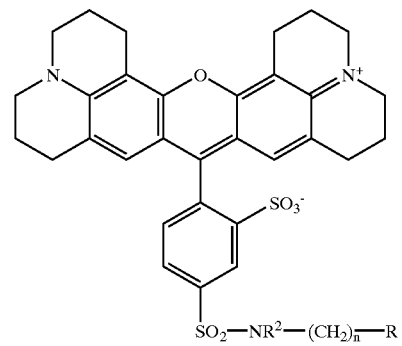

or the general formula

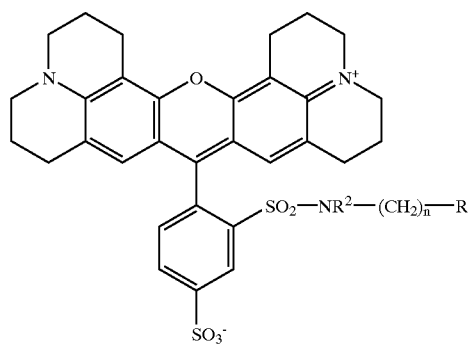

For all dyes, $R^2$ is H, $C_1$–$C_6$ alkyl, or $C_1$–$C_6$ acyl (—(C=O)—R', where R' is H or $C_1$–$C_5$ alkyl); preferably $R^2$ is H, methyl or acetyl. For all dyes, n=1–8 and R is a reactive group that spontaneously reacts with an appropriate functional group to yield a covalent linkage.

For one class of reactive dyes, n=2 to 8, and the reactive group R is a haloacetamide (—NH—(C=O)—CH$_2$—X) or a halomethylbenzamide (—NH—(C=O)—C₆H₄—CH₂—X), where X is Cl, Br or I. Alternatively, R is a maleimide,

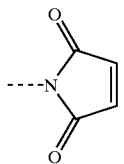

a maleimidyl benzamide

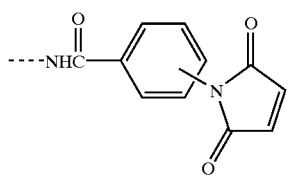

a maleimidyl alkylamido,

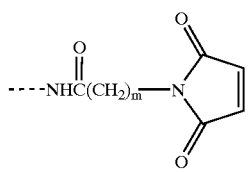

(where m = 1 to 5)

an azidobenzamido,

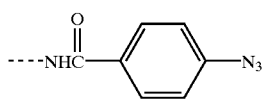

an azidoperfluorobenzamido,

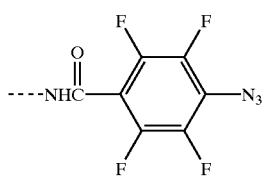

a (3,5-dichloro-2,4,6-triazin-1-yl)amino,

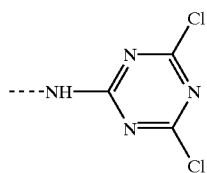

an isocyanato (—N=C=O), or an isothiocyanato (—N=C=S).

In another embodiment of the invention, n is 1 to 7, and the reactive group R is a carboxylic acid (—COOH), or a derivative of a carboxylic acid. An appropriate derivative of a carboxylic acid includes an alkali or alkaline earth metal salt of a carboxylic acid. Alternatively, R is a reactive derivative of a carboxylic acid (—(C=O)—$R_x$), where the reactive group $R_x$ is one that activates the carbonyl group of —(C=O)—$R_x$ toward nucleophilic displacement. In particular, $R_x$ is any group that activates the carbonyl towards nucleophilic displacement without being incorporated into the final displacement product.

Typically, $R_x$ is a good leaving group, selected so as to make R an activated ester of a carboxylic acid: R is optionally a symmetric anhydride that links two sulforhodamine 101 fluorophores, or a simple mixed anhydride of a sulforhodamine 101 fluorophore and a $C_2$–$C_8$ chloroformate, a $C_2$–$C_8$ carboxylic acid or perfluorinated carboxylic acid, a $C_1$–$C_8$ sulfonic or fluorinated sulfonic acid. Alternatively, R is an acyl azide. R is alternatively a carboxylic acid activated by a carbodiimide having 2–14 carbons. Finally, R is an ester of a phenol or a naphthol that is further substituted by at least one strong electron withdrawing group. Selected electron withdrawing groups, present in any combination, include but are not limited to nitro, sulfo, carboxy, alkali or alkaline earth metal salt of sulfo or carboxy, cyano, fluoro or chloro, or trifluoromethyl. Particularly suitable substituted aryl esters include nitrophenyl, sulfophenyl, pentafluorophenyl and pentachlorophenyl esters. Additional R groups include acyl nitrites or acyl hydrazides.

While a variety of activated carboxylic acids and activated esters are suitable for preparing the conjugates of the invention, some are extremely reactive. While a very reactive dye is advantageous for facile preparation of conjugates, they must often be prepared and utilized in situ, as they are not stable enough to be isolated as pure compounds. This class of dyes includes those for which the $R_x$ group is chloride or fluoride, yielding an acid halide. In particular, the class of reactive dyes wherein R is a 1-hydroxybenzotriazole ester are generally too reactive to isolate, although this method of protein conjugation is known in the art. Activated carboxylic acids wherein R is a succinimidyl ester or a sulfosuccinimidyl ester, or the alkali or alkaline earth metal salt of these esters, possess greatly enhanced stability, relative to 1-hydroxybenzotriazole esters, and may be isolated, stored and separated into pure isomers.

Preferred R groups are those that react spontaneously with the functional groups on a biomolecule or other substance, without requiring the presence of a third reagent (such as a catalyst) or unusually harsh conditions, such as very high or low pH, extremes in temperature, organic solvents or other factors.

Synthesis

Reactive dyes that are amine-reactive are generally prepared by the reaction of SSC with an amino acid or its ester-protected derivative (Example 1). The resulting isomers may be separated by chromatographic means at this step or following removal of any protecting groups (e.g. for use as a derivatization reagent in ultra-high resolution separation techniques such as gel or capillary electrophoresis) however, separation is not required or preferred. The dye is converted to an amine-reactive derivative by methods well recognized in the art, such as by conversion to a succinimidyl ester (Example 2), a sulfosuccinimidyl ester (Example 3) or an acyl azide (Example 12). Alternatively, the dye is activated in situ prior to coupling to an amine, for instance by reaction with a water-soluble carbodiimide (Example 3).

The synthesis of haloacetamides, halomethylbenzamides, maleimides, azidobenzamides and 3,5-dichloro-2,4,6-triazines typically utilizes a sulforhodamine 101 sulfonyl cadaverine conjugate, the structure of which is shown below, which is commercially available (TEXAS RED sulfonylcadaverine, Molecular Probes, Eugene Oreg.). Alternatively, any of the $C_2$–$C_8$ homologs of sulforhodamine 101 sulfonyl cadaverine may be used as a starting material (Examples 7–10).

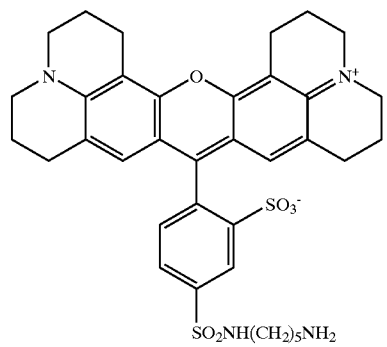

The isocyanate and isothiocyanate derivatives of sulforhodamine 101 are prepared by reaction of sulforhodamine 101 cadaverine (or one of its homologs) with phosgene or thiophosgene, or one of their synthetic equivalents and alternatives, as well documented in the art. Preferably, the isocyanate derivative is synthesized by the Curtius rearrangement of the corresponding acyl azide (Example 12).

Dye-Conjugates

The reactive dyes of the invention are used to label organic substances to form dye-conjugates by the intermolecular reaction of the reactive group on the reactive dye with an appropriate functional group on the organic substance to be conjugated. Appropriate organic substances for conjugation can either be isolated from natural products, prepared synthetically, or isolated from a natural product and then synthetically modified (semi-synthetic). The reactive dyes can label a wide variety of organic substances, provided that the organic substance contains a functional group that possesses suitable reactivity with any one of the reactive groups, R, that are described above. Useable functional groups on the organic substance include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, or carboxylic acids. Amines, thiols, and alcohols are the preferred functional groups for conjugation, as they are both more reactive and more commonly available for the modification of biomolecules. However, a wide variety of other functional groups react under conditions well understood by one skilled in the art (as listed in Table 1). The latter include hydrazine derivatives, hydroxylamine derivatives, thioethers, di- and trisubstituted amines, and carboxylic acids (to form esters). The functional group on the organic substance may be attached directly, or attached via any useful spacer or linker. A dye-conjugate is prepared from either a readily-available organic substance, or from an initially non-reactive organic substance that has been derivatized by an appropriate functional group (as above).

TABLE 1

Examples of some routes to useful conjugations

| REACTIVE GROUP R (attached to reactive dye) | FUNCTIONAL GROUP (attached to organic substance) | YIELDING: (type of conjugation) |
| --- | --- | --- |
| haloacetamides | thiols | thioethers |
| maleimides | thiols | thioethers |
| alkyl halides | thiols | thioethers |

TABLE 1-continued

Examples of some routes to useful conjugations

| REACTIVE GROUP R (attached to reactive dye) | FUNCTIONAL GROUP (attached to organic substance) | YIELDING: (type of conjugation) |
| --- | --- | --- |
| alkyl sulfonates | thiols | thioethers |
| alkyl halides | alcohols/phenols | ethers |
| alkyl sulfonates | alcohols/phenols | ethers |
| carboxylic acids | amines/anilines | carboxamides |
| anhydrides | amines/anilines | carboxamides |
| activated esters* | amines/anilines | carboxamides |
| chlorotriazines | amines/anilines | aminotriazines |
| isocyanates | amines/anilines | ureas |
| isothiocyanates | amines/anilines | thioureas |
| sulfonyl halides | amines/anilines | sulfonamides |
| alkyl halides | amines/anilines | alkyl amines |
| sulfonate esters | amines/anilines | alkyl amines |

*as described previously

Dyes that are selected to conjugate with substances or materials having free amine groups are preferably those dyes of the invention for which R is a succinimidyl or sulfosuccinimidyl ester. Preferably, amine-reactive embodiments have n=4 or 5. Amine-reactive dyes are of particular relevance as they are commonly used to label proteins and polypeptides, which possess free amine groups. Amine-reactive dyes are additionally used to label materials that have been substituted with free amine groups, such as amino-dextrans, or amine containing nucleotides, oligonucleotides or nucleic acids.

Dyes that are selected to conjugate with materials having free thiol groups are preferably those dyes of the invention for which R is a haloacetamide, halomethylbenzamide, or a maleimido group. More preferably, R is an iodoacetamide, maleimido, maleimidylacetamide or a halomethylbenzamide. Preferably, thiol-reactive embodiments have n=5 or 6.

Preferred alcohol- and phenol-reactive dyes are those dyes of the invention for which R is an isocyanate, 3,5-dichloro-2,4,6-triazine, acyl nitrile or is a phosphoramidite. Preferably, alcohol-reactive embodiments have n=5 or 6.

Preferred photoreactive dyes have n=5 or 6, and R is an azidoperfluorobenzamido group.

In one embodiment of the invention, the conjugated substance is an amino acid, peptide, or protein. By amino acid is meant any of the natural amino acids, as well as synthetic variations commonly known and utilized in the art. Common synthetic variations include amino acids that are protected on their amino, carboxylic acid, hydroxy or other functional group. Both peptides and proteins fall under the general category of peptides. While the specific demarcation line between peptides and proteins is not exact, it is typically recognized in the art that peptides have molecular weights of less than about 5,000 to 10,000 daltons, and proteins have molecular weights greater than about 5,000 to 10,000 daltons. Although peptides include molecules as small as dipeptides, the preferred peptides of the invention contain at least five amino acids, more preferably 5 to 36 amino acids. Preferred peptides of the invention include neuropeptides, chemotactic peptides, gastrointestinal peptides, snake toxins, protease substrates, endothelin, protein kinase substrates and others. Proteins typically possess at least secondary structure, and most often tertiary and quaternary structure. The protein conjugates of the present invention tend to be more soluble, and display less fluorescence quenching than the previously known SSC-protein conjugates.

The protein conjugates of the present invention encompass a variety of proteins, including but not limited to enzymes, antibodies, lectins, glycoproteins, lipoproteins, avidin, streptavidin, protein A, protein G and phycobiliproteins. By enzyme is meant any of a group of catalytic proteins that are produced by living cells and that mediate and promote the chemical processes of life without themselves being altered or destroyed. Examples of appropriate enzymes suitable for conjugation include, but are not limited to, peroxidases, proteases, phosphatases, and blycosidases, such as b-D-galactosidases, and b-D-glucuronidases. Antibodies, as used herein, are any of various proteins synthesized by animals in response to the presence of a foreign substance, for example, Immunoglobulin G (IgG) and its fragments. Lectins, as used herein, are any of various proteins that selectively bind carbohydrates, such as cell surface carbohydrates, which can be used to identify cell type. Appropriate lectins are typically isolated from plants, preferably legumes, or from bacteria, fish or invertebrates. A preferred lectin is wheat germ agglutinin. Glycoproteins, as used herein, are any of a class of conjugated proteins containing both carbohydrate and protein units. Phycobiliproteins are any of several proteins isolated from algae, including but not limited to b-phycoerythrin, R-phycoerythrin, C-phycocyanine or allophycocyanin.

In another embodiment of the invention, the conjugated substance is a single base, single nucleoside, single nucleotide or a nucleic acid polymer. By nucleotide is meant the basic structural unit of a nucleic acid, comprising an ester of a nucleoside and one or more phosphoric acid or polyphosphoric acid groups, optionally containing an additional linker or spacer for attachment of a fluorophore or other ligand, such as an alkynyl linkage (U.S. Pat. No. 5,047,519 to Hobbs, Jr. et al., (1991), incorporated by reference) or other linkage (U.S. Pat. No. 4,711,958 to Ward et al., (1987); U.S. Pat. No. 5,175,269 to Stavrianopoulos, (1992); U.S. Pat. No. 5,241,060 to Engelhardt et al., (1993); U.S. Pat. No. 5,328,824 to Ward et al., (1994); all of which are hereby incorporated by reference). The conjugated nucleotide is typically a ribonucleotide, deoxyribonucleotide or a dideoxyribonucleotide. Preferably, the conjugated nucleotide is mono-, di- or triphosphate ester of adenosine, guanosine, uridine or cytidine. More preferably, the conjugated nucleotide is uridine triphosphate or deoxyuridine triphosphate.

Nucleic acid polymers are typically large, chainlike molecules containing phosphoric acids, sugars, and purine and pyrimidine bases. Polymers that are oligonucleotides are typically composed of fewer than 50 nucleotides, more typically composed of fewer than 25 nucleotides. Oligonucleotides are optionally deoxyribonucleic acid polymers (DNA) or ribonucleic acid polymers (RNA), or a hybrid thereof. Suitable oligonucleotides are optionally antisense oligonucleotides, or strands of DNA having a sequence identical to messenger RNA. DNA polymers are optionally single-stranded (ss), double-stranded (ds), triple-stranded or quadruple-stranded DNA. RNA is optionally single-stranded or double-stranded nucleic acid polymers. The nucleic acid polymer may be a natural polymer (biological in origin) or a synthetic polymer (modified or prepared artificially). The nucleic acid polymer optionally incorporates an unusual linker such as morpholine derivatized phosphates (AntiVirals, Inc., Corvallis Oreg.), or peptide nucleic acids such as N-(2-aminoethyl)glycine units (Wittung, et al., NATURE 368, 561 (1994)). In one embodiment of the invention, the dye is attached to the nucleotide, oligonucleotide or nucleic acid polymer via one or more purine or pyrimidine bases through an amide, ester, ether or thioether bond. In another embodiment of the invention, the dye is attached to the phosphate or carbohydrate by a bond that is an ester, thioester, amide, ether or thioether. In one embodiment of the invention, where the conjugated substance is a nucleotide, the reactive group R on the reactive dye is a carboxylic acid, a derivative of a carboxylic acid, or an activated ester of a carboxylic acid. Preferably, the reactive group R is a succinimidyl ester or a sulfosuccinimidyl ester.

In another embodiment of the invention, the conjugated substance is a carbohydrate. By carbohydrate is meant any of the group of organic compounds composed of carbon, hydrogen and oxygen, including sugars, starches and celluloses. In particular, carbohydrates includes polysaccharides such as dextran, FICOL, heparin, glycogen, amylopectin, mannan, inulin, starch, agarose and cellulose. All of these polysaccharides are readily available at low cost, high purity, low background absorbance and fluorescence and have relatively uniform physical properties. Preferably a carbohydrate conjugate is a dextran or ficol conjugate, more preferably a dextran conjugate.

In another embodiment of the invention, the conjugated substance is a lipid. By lipid is meant one of a class of compounds that contains long-chain aliphatic hydrocarbons and their derivatives, such as fatty acids, alcohols, amines, amino alcohols, and aldehydes. The class of lipids include glycolipids, phospholipids and sphingolipids. Glycolipids are lipids that contain carbohydrate units. Phospholipids are lipids containing esters of phosphoric acid containing one or two molecules of fatty acid, an alcohol, and generally a nitrogenous base. Sphingolipids are lipids, such as sphingomyelin, that yield sphingosine or one of its derivatives as a product of hydrolysis. Alternatively, the conjugated substance is a lipid vesicle.

One class of conjugates of the present invention includes conjugates of biologically active molecules. Biologically active molecules include, but are not limited to, cytokines such as lymphokines, hormones, steroids, toxins, or drugs. Alternatively, conjugates of the present invention are conjugates of members of a specific binding pair, such as an antigen or a hapten. In another embodiment, the instant conjugates are conjugates of metabolites, or environmental pollutants.

Another class of conjugates included in the present invention includes conjugates of colorimetric or fluorescent dyes, including but not limited to fluoresceins, rhodamines, resorufins, dipyrrometheneboron difluorides, coumarins, carbocyanines, fluorescent proteins or other fluorophore groups. As an example, the conjugate of phycoerythrin using Compound 2 of the present invention displays an essentially complete energy transfer to the sulforhodamine 101 emission band when the phycoerythrin is illuminated (Example 20). Bifluorophoric dyes comprising dyes of the present invention and other colorimetric or fluorescent dyes will also undergo excited state energy transfer if the two fluorophores possess suitably overlapping spectra and are in close proximity, i.e. where the distance between the fluorophore is about 50 Å.

Alternatively, the conjugates of the present invention are conjugates of cellular systems, cellular fragments, or subcellular particles. Examples of this type of conjugated material include virus particles, bacterial particles, virus components, biological cells, or cellular components. Examples of cellular components that can be labeled, or whose constituent molecules can be labeled, include lysosomes, endosomes, cytoplasm, nuclei, mitochondria, Golgi apparatus and vacuoles.

Finally, the conjugates of the present invention are optionally dye-conjugates of polymers, polymeric particles, polymeric membranes, conducting and non-conducting metals and non-metals, and glass and plastic surfaces and particles.

Conjugates of most low molecular weight drugs, peptides, toxins, nucleotides, phospholipids and other organic molecules are prepared by organic synthesis methods using the reactive dyes of the invention, by means well recognized in the art (Haugland, MOLECULAR PROBES HANDBOOK, supra, Sets 1–7, (1992)). Preferably, conjugation to form a covalent bond consists of simply mixing the reactive dyes of the present invention in a suitable solvent in which both the reactive dye and the substance to be conjugated are soluble. The reaction preferably proceeds spontaneously without added reagents at room temperature or below. For those reactive dyes that are photoactivated, conjugation requires illumination of the reaction mixture to activate the reactive dye. Chemical modification of water insoluble substances, so that a desired dye-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the instant reactive dyes to make them more readily soluble in organic solvents. Particularly useful for labeling substances in aqueous solutions are the sulfosuccinimidyl esters of the present invention (Example 3).

Conjugates of polymers, including biopolymers and other higher molecular weight polymers are typically prepared by means well recognized in the art (for example, Brinkley et al., BIOCONJUGATE CHEM., 3, 2 (1992)). In these cases, a single type of reactive site may be available, as is typical for polysaccharides) or multiple types of reactive sites (e.g. amines, thiols, alcohols, phenols) may be available, as is typical for proteins. Selectivity of labeling is best obtained by choice on an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

Where dye-conjugates are prepared using a photoreactive dye of the invention, such as an azidoacyl derivative, the conjugation requires illumination of the dye by light having a suitable wavelength, typically <400 nm.

When modifying polymers with the dyes, an excess of dye is typically used, relative to the expected degree of dye substitution. Any residual, unreacted dye or a dye hydrolysis product, is typically removed by dialysis, chromatography or precipitation (Example 19). Presence of residual, unconjugated dye can be detected by thin layer chromatography using a solvent that elutes the dye but not its polymer conjugate. In all cases it is usually preferred that the reagents be kept as concentrated as practical so as to obtain adequate rates of conjugation. When the substance to be conjugated is a protein, the preferred protein concentration is 1 to 10 mg/mL.

For soluble dye-conjugates that have multiple attachment sites, the degree of substitution of the polymer is typically determined by first dissolving the dye-free unlabeled polymer in a suitable solvent, and measuring its long wavelength absorption. A determination of the long-wavelength absorption of the labeled dye-conjugate can then be used to determine the approximate degree of substitution of the conjugate, given an approximate value for the extinction coefficient of the sulforhodamine 101 fluorophore. The value that is typically used for the extinction coefficient for the dyes of the present invention for this calculation is 80,000 $cm^{-1}M^{-1}$.

In one aspect of the invention, the conjugate of the invention is associated with an additional substance, that binds to either the sulforhodamine 101 fluorophore or the conjugated substance through noncovalent interaction. In a specific embodiment, the additional substance is an antibody, a lectin, a receptor, an oligonucleotide, a nucleic acid, or a polymer. The additional substance is optionally used to probe for the location of the dye-conjugate, for example, as a means of enhancing the signal of the dye-conjugate.

In another embodiment of the invention, one of the reactive dyes of the invention is provided with instructions for conjugating the dye to any substance possessing an appropriate functional group, and optionally for recovering or purifying the materials labeled thereby. This combination of reactive dye and instructions therefore comprise a kit for labeling a specific substance. In selected embodiments of the invention, the kit thereby formed would possess utility for labeling proteins, oligonucleotides or carbohydrates. The dyes of the present invention are well-suited for the preparation of such a kit, as they possess greatly enhanced stability with respect to SSC, and can therefore more readily be shipped and stored without loss of reactivity.

Applications of the Dye-Conjugates

Typically, the dye-conjugate is a labeled member of a specific binding pair, and is used as a fluorescent probe for the complementary member of that specific binding pair. A specific binding pair member can be a ligand or a receptor. As used in this document, the term ligand means any organic compound for which a receptor naturally exists or can be prepared. A receptor is any compound or composition capable of recognizing a spatial or polar organization of a molecule, e.g. epitopic or determinant site. Ligands for which naturally occurring receptors exist include natural and synthetic proteins, including avidin and streptavidin, antibodies, enzymes, and hormones; nucleotides and natural or synthetic oligonucleotides, including primers for RNA and single- and double-stranded DNA; lipids; polysaccharides and carbohydrates; and a variety of drugs, including therapeutic drugs and drugs of abuse and pesticides. Ligands and receptors are complementary members of a specific binding pair, each specific binding pair member having an area on the surface or in a cavity which specifically binds to and is complementary with a particular spatial and polar organization of the other. Representative specific binding pairs are shown in Table 2.

TABLE 2

| Representative Specific Binding Pairs | |
| --- | --- |
| antigen | antibody |
| biotin | avidin (or streptavidin) |
| IgG* | protein A or protein G |
| drug receptor | drug |
| toxin receptor | toxin |
| carbohydrate | lectin |
| peptide receptor | peptide |
| protein receptor | protein |
| carbohydrate receptor | carbohydrate |
| DNA (RNA) | aDNA (aRNA)† |

*IgG is an immunoglobulin
†aDNA and aRNA are the antisense (complementary) strands used for hybridization In one aspect of the invention, the specific binding pair member is an antibody or antibody fragment, avidin or streptavidin. In this embodiment of the invention, the complementary binding pair member is typically a hapten, an antigen or a biotin. Where the complementary binding pair member is a hapten, the hapten typically has a molecular weight less than 1,000. In another aspect of the invention, the specific binding pair member is an oligonucleotide or nucleic acid polymer. Optionally, the complementary binding pair member is present in a cell, bacteria, virus or yeast cell. Alternatively, the complementary member is immobilized on a solid or semi-solid surface, such as a polymer, polymeric membrane or polymeric particle (such as a latex bead).

Preferably, the fluorescent conjugate of a specific binding pair member is useful for detecting and optionally quantifying the presence of the complementary specific binding pair member in a sample, by methods that are well known in the art. Typically, the fluorescent labeled specific binding pair member is added to a sample that contains, or is thought to contain, the complementary specific binding pair member. Sufficient time is allowed for the two members of the specific binding pair to form a complex, the nature of said complex being dependent upon the type of specific binding pair utilized, but is typically characterized as non-covalent (Van der Waals) interaction. After sufficient time has elapsed, the sample is observed for a colorimetric or fluorescent signal to indicate localization of the fluorescent conjugate. Detection of the complex is typically facilitated by washing or rinsing the sample to remove uncomplexed dye-conjugate.

While the resulting complex is detectable colorimetrically, using ambient light, typically the complex is detected by the fluorescence properties of the labeled specific binding pair member. Upon illumination, such as by an ultraviolet or visible wavelength emission lamp, an arc lamp, a laser, or even sunlight or ordinary room light, the labeled conjugates and specific binding pair complexes display intense visible absorption as well as fluorescence emission. Selected equipment that is useful for illuminating the dye-conjugates of the invention includes, but is not limited to, hand-held ultraviolet lamps, mercury arc lamps, xenon lamps, argon lasers, and YAG lasers. These illumination sources are optionally integrated into laser scanners, fluorescence microtiter plate readers, standard or mini fluorometers, or chromatographic detectors. This colorimetric absorbance or fluorescence emission is optionally detected by visual inspection, or by use of any of the following: CCD cameras, video cameras, photographic film, laser scanning devices, fluorometers, photodiodes, quantum counters, epifluorescence microscopes, scanning microscopes, flow cytometers, fluorescence microtiter plate readers, or by means for amplifying the signal such as photomultiplier tubes. Where the sample is examined using a flow cytometer, a fluorescence microscope or a fluorometer, the instrument is optionally used to distinguish and discriminate between the dye-conjugate and a second fluorophore with detectably different optical properties, preferably, by distinguishing the fluorescence response of the dye-conjugate from that of the second fluorophore. Where the sample is examined using a flow cytometer, examination of the sample optionally includes sorting the specific binding pair complex based on the fluorescence response of the dye-conjugate.

It is also possible to utilize the dyes to label reactive sites such as occur at the surface of cells, in cell membranes or in intracellular compartments such as organelles, or in the cell's cytoplasm. Among the preferred reagents are those that react selectively with intracellular glutathione (Example 10, Compound 8). Other fluorescent probes that react with intracellular glutathione have previously been described (U.S. Pat. No. 5,362,628 to Haugland et al, (1994); Copending application HALOALKYL DERIVATIVES OF REPORTER MOLECULES USED TO ANALYZE METABOLIC ACTIVITY IN CELLS, U.S. Pat. No. 5,576,424 to Haugland et al. (1996)).

In addition to their utility as a labeled specific binding pair member, conjugates prepared from any of the reactive dyes can also be used for a variety of other purposes, including any purposes that have been described for conjugates of SSC. Primary applications include those in immunofluorescence, fluorescence in situ hybridization, labeling of receptors with a low or high molecular weight fluorescent analog, conjugation to proteins or carbohydrates for microinjection into cells, and the tracing of labeled cells or polymers. The nucleotide conjugates of the present invention are readily incorporated by DNA polymerase and can be used for in situ hybridization or other techniques (Example 32). Also, the reactive dyes can be used to derivatize low molecular weight compounds for their analysis by CZE, HPLC or other separation techniques.

The examples below are given so as to illustrate the practice of this invention. They are not intended to limit or define the entire scope of this invention.

EXAMPLES

Example 1

Preparation of 6-(4(or 2)-(9-(2,3,6,7,12,13,16,17-octahydro-1H,5H-11H,15H-xantheno(2,3,4-ij:5,6,7-i'j')diquinolizinyl-18-ium))-3(or 5)-sulfo-1-phenylsulfonamido)hexanoic acid (Compound 1)

The following mixture of compounds is prepared:

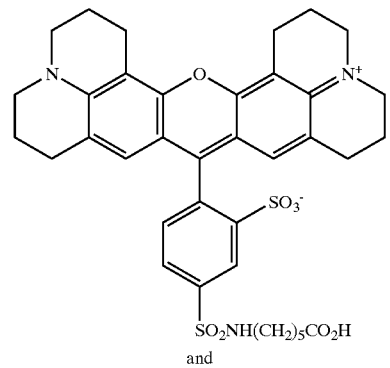

and

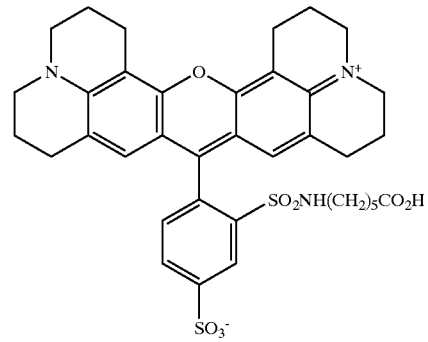

To a solution of 0.60 g (3.30 mmol) of 6-aminohexanoic acid methyl ester and 1.0 mL of triethylamine in 50 mL of chloroform is added 1.50 g (2.40 mmol) of SSC in small portions over a period of 10 minutes while the reaction mixture is stirred at 0° C. After the reaction mixture is stirred at room temperature 15 hours, it is washed with three 50 mL portions of water. The organic layer is separated, dried over anhydrous sodium sulfate and concentrated under reduced pressure to give a dark purple solid. This crude methyl ester derivative is purified by chromatography on silica gel with 2.5% methanol in chloroform as eluant to give 1.20 g (68%) of the methyl ester.

To a suspension of 0.80 g (1.09 mmol) of the above methyl ester in 15 mL of dioxane is added 25 mL of 6 M HCl dropwise over a period of 5 minutes. After the reaction mixture is stirred at room temperature for 18 hours, it is poured into 200 mL of water. The resulting solid is collected by filtration and purified by chromatography on silica gel with 15% methanol in chloroform as eluant. A dark purple solid (620 mg, 79%) is obtained as a mixture of two isomers. TLC: $R_f$=0.54 (silica gel, 25% methanol in chloroform). $^1$H NMR (DMSO-$d_6$): δ=8.40 (d, 1H, ArH), 7.95–7.84 (m, 1H, ArH), 7.36 (d, 1H, ArH), 6.55 (d, 2H, ArH), 3.60–3.40 (m, 8H, $CH_2$), 3.15–2.58 (m, 8H, $CH_2$), 2.20 (m, 8H, $CH_2$), 1.50–1.12 (m, 6H, $CH_2$). Absorption maximum: 591 nm (ε=85,400 $cm^{-1}M^{-1}$) in pH 7.5 phosphate buffer, 584 nm (e=94,400 $cm^{-1}M^{-1}$) in methanol, emission maximum: 610 nm in pH 7.5 phosphate buffer solution, 603 nm in methanol.

The two mixed isomers are resolved by HPLC under the following conditions: Microsorb MV 86-800-D5, CN-Si column, 5μ, 4.6 mm id×25 cm length (Rainin, Woburn, Mass.); eluted with acetontrile (1)/methanol (1)-0.1 M TEAA (triethylammonium acetate), pH 7.0, 5/95, flow rate 1 mL/min, Isomer I; retention time of 22.40 minutes, absorption maximum: 588 nm in pH 7.5 phosphate buffer, 581 nm in methanol, emission maximum: 607 nm in pH 7.5 phosphate buffer, 599 nm in methanol. Isomer II; retention time of 23.68 minutes, absorption maximum: 590 nm in pH 7.5 phosphate buffer, 583 nm in methanol, emission maximum: 612 nm in pH 7.5 phosphate buffer, 602 nm in methanol.

Example 2

Preparation of a Succinimidyl Ester of Sulforhodamine 101 (Compound 2)

The following mixture of compounds is prepared:

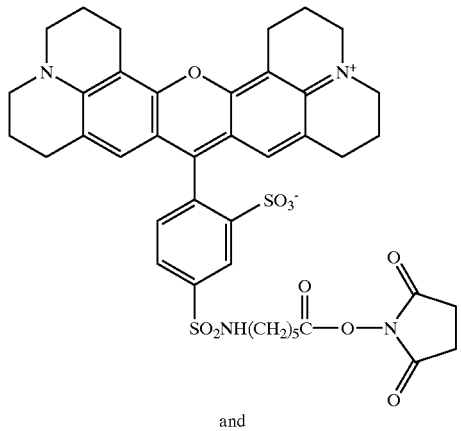

and

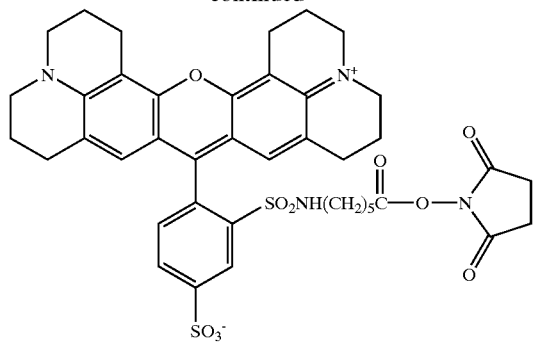

To a solution of 300 mg (0.42 mmol) of Compound 1 (Example 1) in 3 mL of DMF is added 70 μL (0.50 mmol) of triethylamine, followed by addition of 150 mg (0.50 mmol) of O-(N-succinimidyl)-N,N,N',N'-tetramethyluronium tetrafluoroborate. After the reaction mixture is stirred at room temperature for 1 hour, it is diluted with 50 mL of chloroform, washed with water, dried over anhydrous sodium sulfate and concentrated under reduced pressure to give a solid. This solid is dissolved in 10 mL of chloroform. The resulting solution is added dropwise into 100 mL of ether while stirring vigorously at room temperature. The resulting precipitate is collected by filtration and dried under vacuum to give 295 mg (87%) of a dark purple solid as mixed isomers. TLC: $R_f$=0.20 (silica gel, 10% methanol in chloroform: $^1$H NMR (DMSO-$d_6$): δ=8.39 (d, 1H, ArH), 7.92–7.84 (m, 1H, ArH), 7.48–7.33 (m, 1H, ArH), 6.53 (d, 2H, ArH), 3.54–3.40 (m, 8H, $CH_2$), 3.13–2.57 (m, 8H, $CH_2$), 2.80 (s, 4H, $CH_2$), 2.08–1.74 (m, 8H, $CH_2$), 1.65–1.12 (m 6H, $CH_2$). Absorption maximum: 591 nm in pH 7.5 phosphate buffer, 582 nm in methanol; emission maximum: 611 nm in pH 7.5 phosphate buffer, 603 nm in methanol.

The chemical reactivity of this succinimidyl ester is demonstrated by thin layer chromatography. n-Butylamine reacts with the succinimidyl ester to form a new product with $R_f$=0.27 (silica gel, 10% methanol in chloroform).

Example 3

Preparation of a Sulfosuccinimidyl Ester of Sulforhodamine 101 (Compound 3)

The following mixture of compounds is prepared:

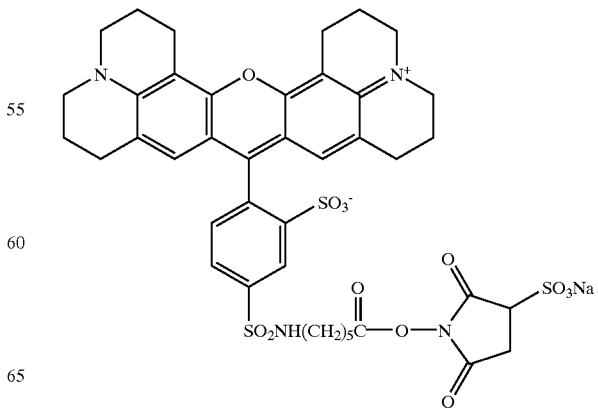

-continued
and

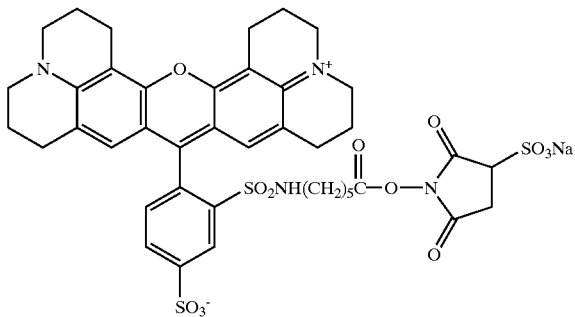

To a solution of 50 mg (0.07 mmol) of Compound 1 (Example 1) and 17 mg (0.08 mmol) of N-hydroxysulfosuccinimide, sodium salt in 2 mL of DMF is added 15 μL (0.09 mmol) of N,N'-diisopropylcarbodiimide. After the reaction mixture is stirred at room temperature for 24 hours, it is added to 20 mL of isopropyl alcohol. The resulting precipitate is removed by filtration and the filtrate is concentrated under reduced pressure to remove most of the isopropanol. The residual DMF solution is poured into 30 mL of ether to precipitate the product. The resulting precipitate is collected by filtration to give 32 mg (50%) of the sulfosuccinimidyl ester as a dark purple solid. TLC: $R_f$=0.20 (silica gel, 25% methanol in chloroform). $^1$H NMR (DMSO-$d_6$): δ=8.40 (d, 1H, ArH), 7.90–7.84 (m, 1H, ArH), 7.48–7.33 (m, 1H, ArH), 6.53 (d, 2H, ArH), 3.95–3.90 (m, 1H, CH), 3.77–3.70 (m, 2H, CH$_2$), 3.55–1.12 (s, 34H, CH$_2$). Absorption maximum: 591 nm in pH 7.5 phosphate buffer, 584 nm in methanol; emission maximum: 611 nm in pH 7.5 phosphate buffer, 604 nm in methanol.

The reactivity of this sulfosuccinimidyl ester is demonstrated by thin layer chromatography. n-Butylamine reacts with this sulfosuccinimidyl ester to form a new product with $R_f$=0.57 (silica gel, 25% methanol in chloroform).

Example 4

Preparation of a Nucleotide Conjugate of Sulforhodamine 101

To a solution of 3 mg of 5-(3-aminoallyl)-2'-deoxyuridine-5'-triphosphate, ammonium salt (Sigma Chemical) in 300 μL of water is added a solution of 4 mg of Compound 2 (Example 2) in 200 μL of DMF, followed by addition of 5 μL of triethylamine. After the mixture is stirred at room temperature for 3 hours, it is purified by chromatography over lipophilic SEPHADEX resin using water for elution. The desired fractions are combined and lyophilized to give 3 mg of the fluorescent nucleotide conjugate as a dark purple solid.

Example 5

Preparation of an Oligonucleotide Conjugate of Sulforhodamine 101

A sample of 500 μg of a 5'-amine modified, 24-base M13 primer sequence is dissolved in 220 μL of 0.1 M borated sodium bicarbonate pH 8.5 aqueous buffer in the microcentrifuge tube. To this oligonucleotide solution is added a solution of 1 mg of Compound 3 (Example 3) in 35 μL of DMF. The reaction mixture is shaken by hand for a few minutes and allowed to stand at room temperature for 16 hours. To the mixture is added 15 μL of 5 M NaCl and 3 volumes of cold 100% ethanol. The resulting mixture is incubated at –20° C. for 30–60 minutes, and then microcentrifuged for 15–30 minutes at 4° C. (5,000–10,000 g). After microcentrifugation, the ethanol supernate is decanted, and the pellet is resuspended in 100 μL H$_2$O. The labeled oligonucleotide is then purified by HPLC on a 220 mm×10 mm 300 Å C8 reverse phase column (Rainin Instrument Co., Woburn, Mass.) using the following gradient: Solvent A—0.1 M TEAA (pH~7), Solvent B—acetonitrile. Ramp Solvent B from 15% to 60% over 30 minutes. Detection is accomplished using a Waters 490 dual wavelength UV-Vis detector monitoring 254 nm and 590 nm. The desired peak is collected and evaporated to give approximately 200 μg of the fluorescent oligonucleotide.

A comparison of labeling efficiency of both SSC and Compound 2 when conjugating an M13 primer using the procedure given above shows that Compound 2 labels the oligonucleotide approximately two-fold more efficiently than SSC, as determined by comparing the ratio of the integrated absorbance of the product peaks to that of the unlabeled oligonucleotide during HPLC.

Example 6

Preparation of a Phalloidin Conjugate
(Compound 4)

To a solution of 3 mg of aminophalloidin p-toluenesulfonate and 4 mg of Compound 2 (Example 2) in 300 μL of DMF is added 5 μL of triethylamine and the mixture is stirred at room temperature for 1 hour. To the reaction mixture is added 7 mL of ether and the resulting precipitate is collected by centrifugation. The crude product is purified by chromatography over lipophilic SEPHADEX resin using water for elution. The desired fractions are combined and lyophilized to give 4 mg of a dark purple solid as a fluorescent phalloidin conjugate.

Example 7

Preparation of an Iodoacetamide-modified Sulforhodamine 101, Compound 5

The following mixture of compounds is prepared:

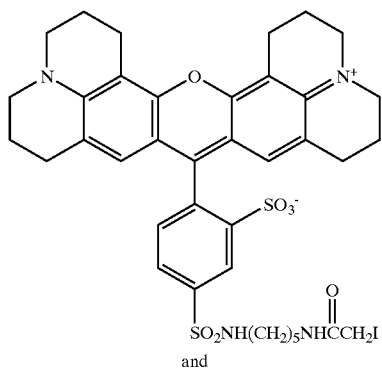
and

19
-continued

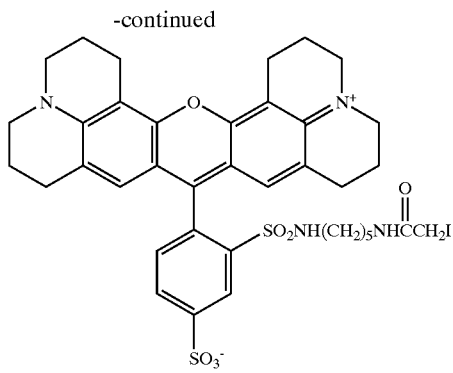

To a suspension of 50 mg (0.07 mmol) of sulforhodamine 101 sulfonyl cadaverine in 10 mL of chloroform is added 15 μL (0.09 mmol) of N,N-diisopropylethylamine, followed by addition of 20 mg (0.07 mmol) of succinimidyl iodoacetamide and the mixture is stirred at room temperature for 18 hours. The reaction mixture is then diluted with 50 mL of chloroform, washed with water (3×50 mL), dried over anhydrous sodium sulfate and concentrated under reduced pressure to give a crude product. The product is purified by chromatography on silica gel with 5% methanol in chloroform as eluant to give 14 mg (23%) of the iodoacetamide as a dark purple solid. TLC: $R_f$=0.21 (silica gel, 10% methanol in chloroform). $^1$H NMR (DMSO-$d_6$): δ=8.38 (d, 1H, ArH), 7.90–7.80 (m, 1H, ArH), 7.38–7.35 (m, 1H, ArH), 6.50 (d, 2H, ArH), 3.60 (s, 2H, $CH_2$I), 3.58–3.40 (m, 8H, $CH_2$), 3.05 (m, 6H, $CH_2$), 2.68–2.54 (m, 6H, $CH_2$), 2.08–1.98 (m, 4H, $CH_2$), 1.90–1.78 (m, 4H, $CH_2$), 1.45–1.12 (m, 6H, $CH_2$). Absorption maximum: 591 nm in pH 7.5 phosphate buffer, 584 nm in methanol; emission maximum: 613 nm in pH 7.5 phosphate buffer, 603 nm in methanol.

The chemical reactivity of this iodoacetamide is demonstrated by thin layer chromatography. N-Acetylcysteine reacts with this iodoacetamide to form a new product with $R_f$=0.08 (silica gel, 25% methanol in chloroform).

Example 8

Preparation of Bromoacetamide Modified Sulforhodamine 101, Compound 6

The following mixture of compounds is prepared:

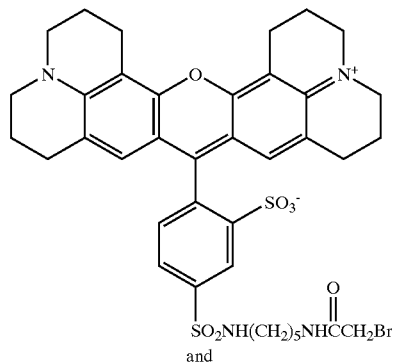
and

20
-continued

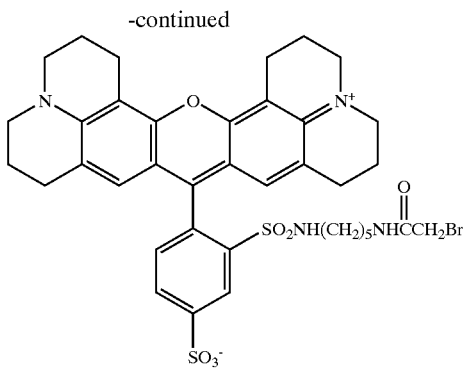

To a suspension of 50 mg (0.07 mmol) of sulforhodamine 101 sulfonyl cadaverine in 10 mL of chloroform is added 15 μL (0.09 mmol) of N,N-diisopropylethylamine, followed by addition of 7 μL (0.08 mmol) of bromoacetyl bromide and the reaction mixture is stirred at room temperature for 5 hours. It is then diluted with 50 mL of chloroform, washed with water (3×50 mL), dried over anhydrous sodium sulfate and concentrated under reduced pressure to give a crude product. The product is purified by chromatography on silica gel with 5%. methanol in chloroform as eluant to give 41 mg (73%) of the bromoacetamide as a dark purple solid. TLC: $R_f$=0.20 (silica gel, 10% methanol in chloroform). $^1$H NMR (DMSO-$d_6$): δ=8.38 (d, 1H, ArH), 7.91–7.80 (m, 1H, ArH), 7.40–7.35 (m, 1H, ArH), 6.50 (d, 2H, ArH), 3.80 (s, 2H, $CH_2$Br), 3.60–3.40 (m, 8H, $CH_2$), 3.06–2.83 (m, 6H, $CH_2$), 2.67–2.53 (m, 6H, $CH_2$), 2.09–1.97 (m, 4H, $CH_2$), 1.90–1.78 (m, 4H, $CH_2$), 1.44–1.12 (m, 6H, $CH_2$). Absorption maximum: 591 nm in pH 7.5 phosphate buffer, 583 nm in methanol; emission maximum: 610 nm in pH 7.5 phosphate buffer, 603 nm in methanol.

The chemical reactivity of this bromoacetamide is demonstrated by thin layer chromatography. N-acetyl cysteine reacts with this bromoacetamide to form a new product with $R_f$=0.08 (silica gel, 25% methanol in chloroform).

Example 9

Preparation of a Maleimide-modified Sulforhodamine 101, Compound 7

The following mixture of compounds is prepared:

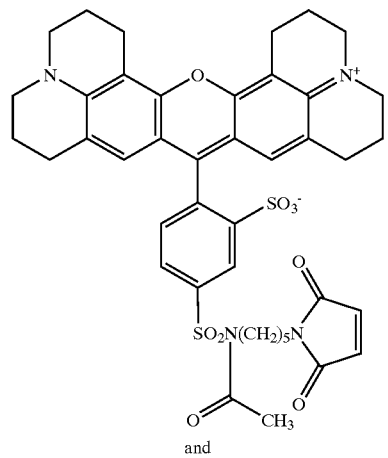
and

21
-continued

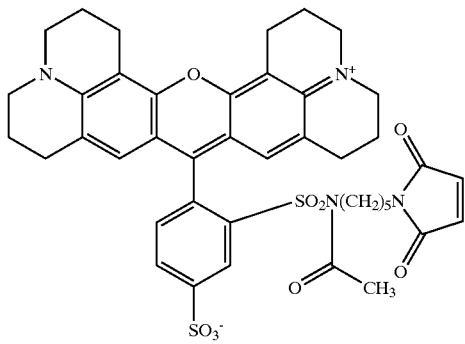

To a solution of 50 mg (0.07 mmol) of sulforhodamine 101 sulfonyl cadaverine and 25 µL (0.14 mmol) of N,N-diisopropylethylamine in 5 mL of chloroform is added 10 mg (0.10 mmol) of maleic anhydride. After the reaction mixture is stirred at room temperature for 5 hours, it is concentrated to a volume of 1 mL under reduced pressure. The residual solution is poured into 10 mL of ether. The resulting precipitate is collected by filtration to give 43 mg of the maleamic acid intermediate as a dark purple solid.

A suspension of this intermediate and 10 mg of sodium acetate in 2 mL of acetic anhydride is heated at 90° C. After 30 minutes the reaction mixture is concentrated under reduced pressure. The residue is diluted with 50 mL of chloroform, washed with water (3×50 mL), dried over anhydrous sodium sulfate and concentrated under reduced pressure to give a crude product. The crude product is purified by chromatography on silica gel with 5% methanol in chloroform as eluant to give 18 mg (32%) of a maleimide as mixed isomers. For analytical purposes, small portions of this sample are further purified by preparative thin layer chromatography on silica gel using 10% methanol in chloroform as eluant. Two isomers are separated. Isomer 1; TLC: $R_f$=0.15 (silica gel, 10% methanol in chloroform); Absorption maximum: 590 nm in pH 7.5 phosphate buffer, emission maximum: 610 nm in pH 7.5 phosphate buffer; $^1$H NMR (DMSO-$d_6$): δ=8.42 (s, 1H, ArH), 8.06 (d, 1H, ArH), 7.42 (d, 1H, ArH), 7.01 (d, 2H, —CH=CH—), 6.50 (s, 2H, ArH), 3.50–1.18 (m, 34H, $CH_2$), 2.37 (s, 3H, $CH_3$). Isomer 2; TLC: $R_f$=0.13 (silica gel, 10% methanol in chloroform); Absorption maximum: 601 nm in pH 7.5 phosphate buffer; emission maximum: 619 nm in pH 7.5 phosphate buffer; $^1$H NMR (DMSO-$d_6$): δ=8.41 (s, 1H, ArH), 8.08 (d, 1H, ArH), 7.44 (d, 1H, ArH), 7.01 (d, 2H, —CH=CH—), 6.44 (s, 2H, ArH), 3.58–1.19 (m, 34H, $CH_2$), 1.97 (s, 3H, $CH_3$).

The chemical reactivity of this maleimide is demonstrated by thin layer chromatography. N-acetyl cysteine reacts with this maleimide to form a new product with $R_f$=0.10 (silica gel, 25% methanol in chloroform).

22

Example 10

Preparation of a Chloromethylbenzamide Modified Sulforhodamine 101, Compound 8

The following mixture of compounds is prepared:

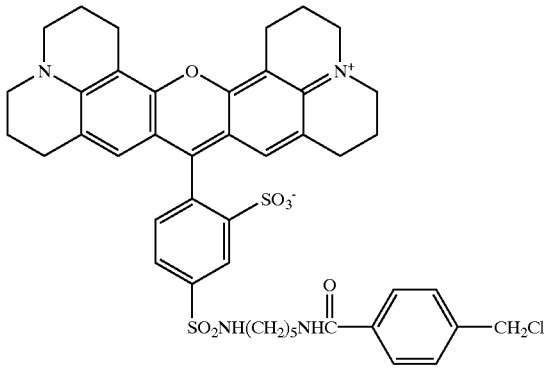

and

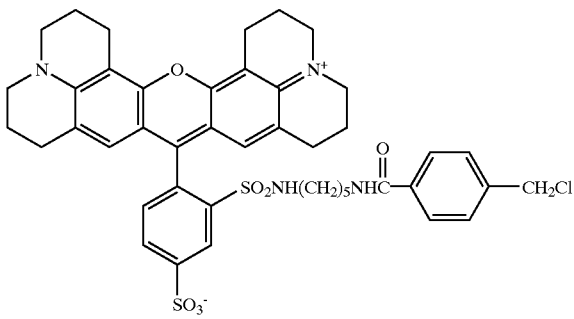

To a solution of 100 mg (0.14 mmol) of sulforhodamine 101 sulfonyl cadaverine and 45 µL (0.32 mmol) of triethylamine in 30 mL of chloroform is added 20 mg (0.16 mmol) of 4-(chloromethyl)benzoyl chloride. After the reaction mixture is stirred at room temperature for 3 hours, it is washed with water (3×30 mL), dried over anhydrous sodium sulfate and concentrated under reduced pressure to give a crude product. This crude product is purified by chromatography on silica gel with 5% methanol in chloroform as eluant to give 97 mg (79%) of a pure product as mixed isomers. $^1$H NMR (DMSO-$d_6$): δ=8.40 (d, 1H, ArH), 7.98–7.90 (m, 1H, ArH), 7.78 (d, 2H, ArH), 7.42 (d, 2H, ArH), 7.33 (d, 1H, ArH), 6.50 (s, 2H, ArH), 4.80 (s, 2H, $CH_2Cl$), 3.54–1.21 (m, 34H, $CH_2$). For analytical purposes, small portions of this product are further separated by preparative thin layer chromatography on silica gel using 10% methanol in chloroform as eluant. Two isomers are separated. Isomer 1: $R_f$=0.18 (silica gel, 10% methanol in chloroform), absorption maximum: 589 nm in pH 7.5 phosphate buffer, emission maximum 608 nm in pH 7.5 phosphate buffer. Isomer 2: $R_f$=0.16 (silica gel, 10% methanol in chloroform), absorption maximum: 591 nm in pH 7.5 phosphate buffer; emission maximum: 612 nm in pH 7.5 phosphate buffer.

Example 11

Preparation of a Phospholipid Modified Sulforhodamine 101, Compound 9

The following mixture of compounds is prepared:

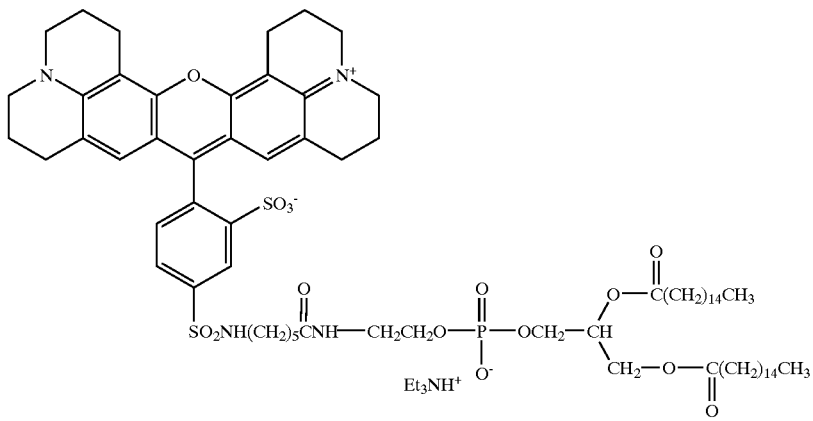

and

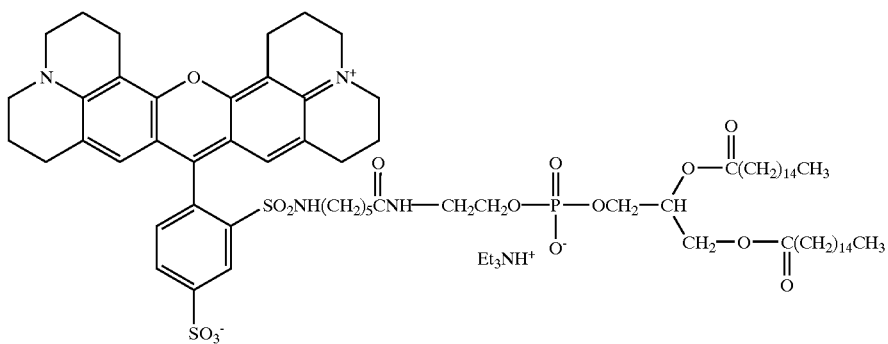

To a solution of 200 mg (0.24 mmol) of Compound 2 (Example 2) in 50 mL of chloroform is added 35 μL (0.25 mmol) of triethylamine, followed by addition of 170 mg (0.24 mmol) of 1,2-dipalmitoyl-sn-glycero-3-phosphoethanolamine. After the reaction mixture is stirred at room temperature for 24 hours, it is concentrated under reduced pressure. The resulting crude product is purified by chromatography on silica gel with 15% methanol in chloroform as eluant to give 290 mg (79%) of the product as mixed isomers. TLC: $R_f$=0.33 (silica gel, 25% methanol in chloroform). $^1$H NMR: (DMSO-$d_6$): δ=8.49 (d, 1H, ArH), 7.97–7.40 (m, 1H, Arh), 7.32 (d, 1H, ArH), 6.49 (d, 2H, ArH), 5.14–5.07 (m, 1H, CH), 4.34–1.14 (m, 104H, CH$_2$), 1.06 (t, 9H, CH$_3$), 0.85 (t, 6H, CH$_3$). TLC: absorption maximum: 583 nm in methanol; emission maximum: 602 nm in methanol.

Example 12

Preparation of an Acylazide Derivative of Sulforhodamine 101, Compound 10

The following mixture of compounds is prepared:

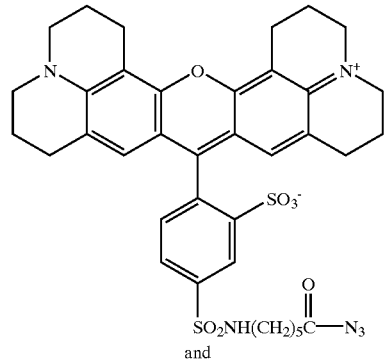

and

-continued

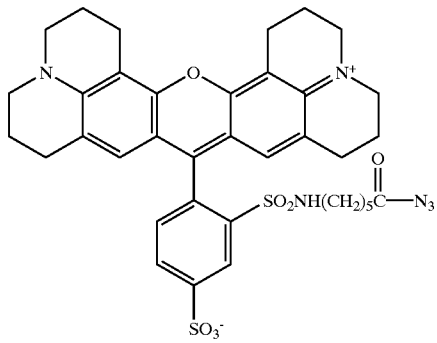

To a solution of 50 mg (0.07 mmol) of Compound 1 (Example 1) and 20 μL (0.14 mmol) of triethylamine in 5 mL of 1,2-dichloroethane is added 20 μL (0.09 mmol) of diphenylphosphoryl azide. After stirring at room temperature for 18 hours, the reaction mixture is subjected to column chromatography on silica gel with 5% methanol in chloroform as eluant. From the desired combined fractions 29 mg (60%) of a product as mixed isomers is obtained.

The reactive isocyanate derivative of sulforhodamine 101 is prepared from Compound 10 by a Curtius rearrangement of the acyl azide, followed by reaction with an appropriate alcohol. For example, a solution of 10 mg of acyl azide and 5 mg of cholesterol in 5 mL of dry 1,2-dichloroethane is heated under reflux in a stream of $N_2$ for 2 hours. After the reaction mixture is cooled to room temperature, thin layer chromatography on silica gel is analyzed to show a new spot for a fluorescent cholesterol conjugate (Compound 11).

Example 13

Preparation of an Isothiocyanate Derivative of Sulforhodamine, Compound 12

The following mixture of compounds is prepared:

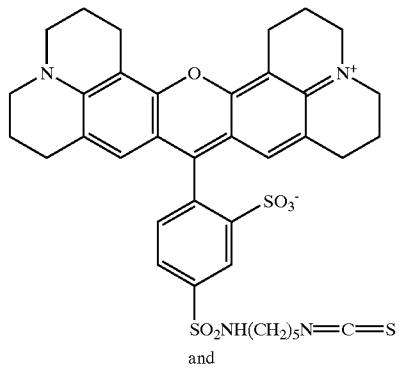

and

-continued

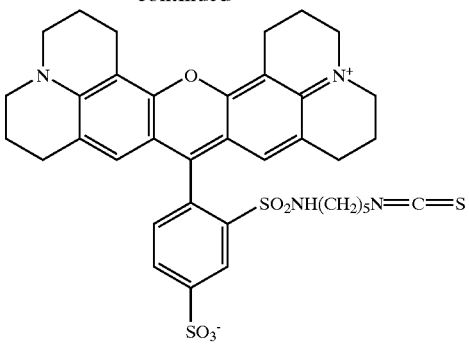

To a solution of 50 mg (0.07 mmol) of sulforhodamine 101 sulfonyl cadaverine in 10 mL of dichloromethane is added 17 mg (0.07 mmol) of 1,1'-thiocarbonyldi-2(1H)-pyridone. After stirring at room temperature for 1 hour, the reaction mixture is washed with water (2×10 mL), dried over anhydrous sodium sulfate and concentrated under reduced pressure to give 41 mg (80%) of a product as a dark purple solid. This isothiocyanate reacts with n-butylamine to give a new spot on thin layer chromatography.

Example 14

Preparation of a Dichlorotriazine Derivative of Sulforhodamine 101, Compound 13

The following mixture of compounds is prepared:

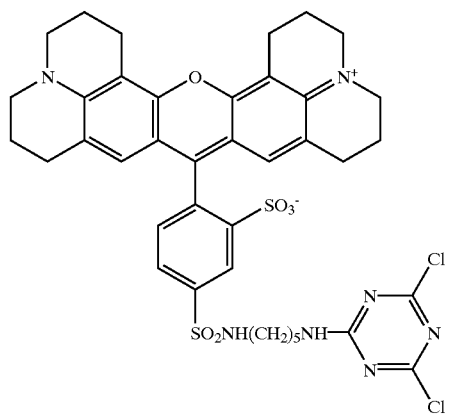

and

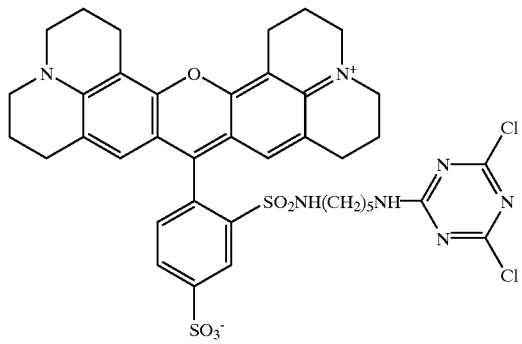

To a suspension of 15 mg (0.08 mmol) of cyanuric chloride in 2 mL of chloroform is added a solution of 50 mg (0.07 mmol) of sulforhodamine 101 sulfonyl cadaverine in 2 mL of methanol while the mixture is stirred in an ice-water bath. After stirring at an ice-water bath temperature for 1 hour, the reaction mixture is poured into 15 mL of ether. The resulting precipitate is collected by filtration to give 45 mg (70%) of a desired product as a dark purple solid.

Example 15

Preparation of a Maleimide-modified Sulforhodamine 101, Compound 14

The following mixture of compounds is prepared:

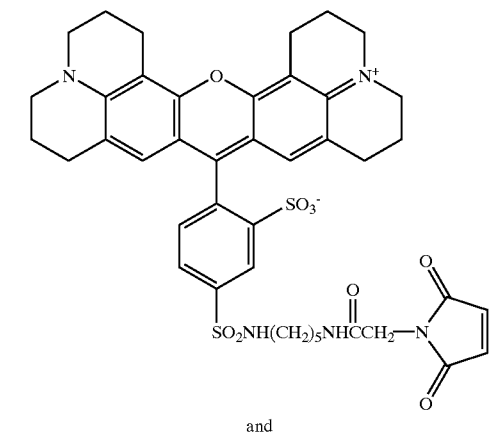

and

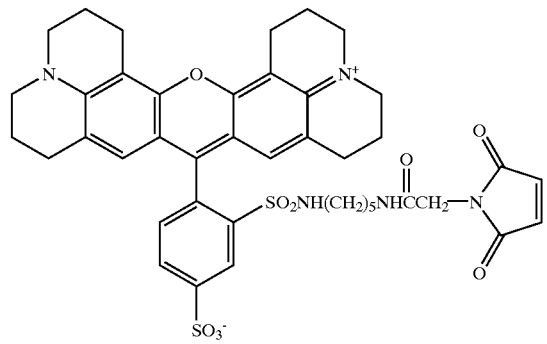

To a solution of 55 mg (0.08 mmol) of sulforhodamine 101 sulfonyl cadaverine and 12 µL (0.08 mmol) of triethylamine in 15 mL of chloroform is added 20 mg (0.08 mmol) of succinimidyl maleimidylacetate. After the reaction mixture is stirred at room temperature for 3 hours, it is washed with water (2×15 mL), dried over anhydrous sodium sulfate and concentrated under reduced pressure to give a crude product. This crude product is purified by chromatography on silica gel with 3% methanol in chloroform as eluant to give 35 mg (53%) of the pure product as a mixture of isomers: $R_f$=0.20 (silica gel, 10% methanol in chloroform), absorption maximum: 583 nm in methanol; emission maximum: 602 nm in methanol.

Example 16

Preparation of an Azide-modified Sulforhodamine 101, Compound 15

The following mixture of compounds is prepared:

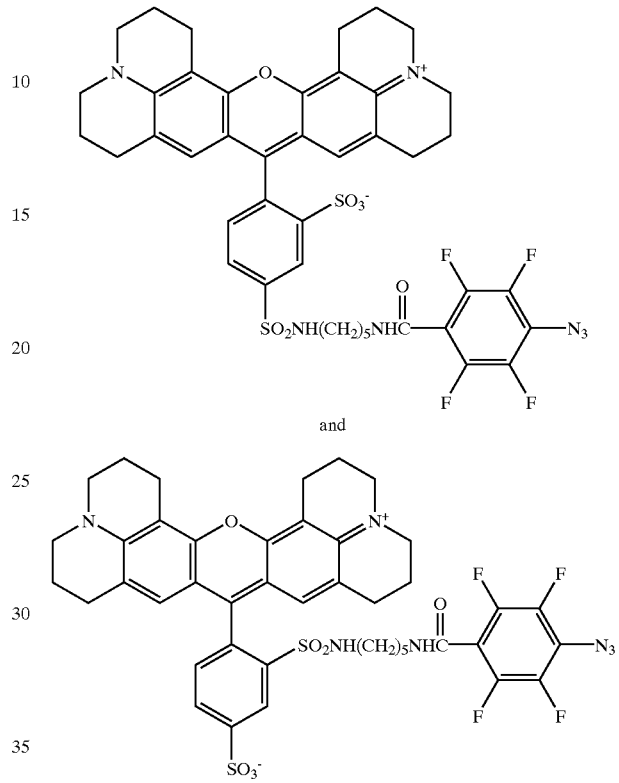

To a solution of 25 mg (0.04 mmol) of sulforhodamine 101 sulfonyl cadaverine and 6 µL (0.04 mmol) of triethylamine in 10 mL of chloroform is added 14 mg (0.04 mmol) of 4-azido-2,3,5,6-tetrafluorobenzoic acid, succinimidyl ester. After the reaction mixture is stirred at room temperature for 4 hours, it is washed with water (2×10 mL), dried over anhydrous sodium sulfate and concentrated under reduced pressure to give a crude product. This crude product is purified by chromatography on silica gel with 3% methanol in chloroform as eluant to give 21 mg (65%) of the desired product as a dark purple solid.

Example 17

Preparation of a Drug Conjugate of Sulforhodamine 101, Compound 16

A fluorescent dopamine $D_2$ antagonist is prepared as follows:

To a solution of 10 mg (0.02 mmol) of N-(p-aminophenethyl)spiperone, which is prepared as described in Amlaiky, et al., FEBS LETT, 176, 436 (1984), and 10 µL (0.06 mol) of N,N-diisopropylethylamine in 1 mL of DMF is added 15 mg (0.02 mmol) of Compound 12 (Example 13). After the reaction mixture is stirred at room temperature for 3 hours, it is poured into 5 mL of ether. The resulting precipitate is collected by centrifugation. This crude product is purified by chromatography on silica gel using 10% methanol in chloroform to give 21 mg (85%) of a pure product as a dark purple solid.

Example 18

Preparation of a Peptide Conjugate of Sulforhodamine 101, Compound 17

To a suspension of 5 mg of an N-formyl modified hexapeptide (a potent chemoattractant for human neutrophils, Niedel et al. SCIENCE, 205, 1412 (1979) in 500 µL of DMF is added 3 µL of triethylamine followed by the addition of 5 mg of Compound 2 (Example 2) and the whole reaction mixture is stirred at room temperature for 1 hour. The reaction mixture is purified by chromatography over lipophilic SEPHADEX resin using water for elution. The desired fractions are combined and lyophilized to give 5 mg of the fluorescent hexapeptide.

Example 19

Protein Conjugates of Sulforhodamine 101

Protein conjugates of sulforhodamine 101 are prepared using Compound 2 (Example 2). The degree of substitution achieved on the selected proteins (bovine serum albumin (BSA), goat anti-mouse IgG (GAM) or streptavidin (STR)) is then determined.

A fresh solution of the desired protein is prepared that is 10 mg protein/mL in 0.1 M sodium bicarbonate. The labeling reagent (Compound 2) is dissolved in DMF to give a concentration of 10 mg dye/mL. Predetermined amounts of the labeling reagent in DMF are slowly added to the protein solution with stirring. A molar ratio of 10 equivalents dye to equivalent of protein is typical, though the optimal amount varies with particular labeling reagent and protein being labeled. The reaction mixture is incubated at room temperature for one hour. The dye-protein conjugate is separated from free unreacted reagent by gel filtration on a CELLUFINE GH-25 column equilibrated in PBS. The initial, protein-containing colored band is collected from the column, and the degree of substitution is determined by measuring the absorbance of the conjugate at 595 nm, and calculating the degree of substitution using an extinction coefficient of 80,000 cm$^{-1}$M$^{-1}$ for the dye.

Dye conjugates are similarly prepared using SSC excepting that the protein solution is maintained at pH 9, and the labeling reaction is conducted at ice bath temperatures to minimize hydrolysis of the labeling reagent.

The degree of substitution achieved with each labeling reagent on the selected protein is shown in the following table:

| Protein | SSC | | Compound 2 | |
|---|---|---|---|---|
| | Dye:Protein Ratio | Degree of Substitution | Dye:Protein Ratio | Degree of Substitution |
| bovine serum albumin (BSA) | 15 | 3.2 | 15 | 4.5 |
| goat anti-mouse (GAM) | 2.5 | 0.57 | 2.5 | 1.29 |
| | 5.5 | 1.0 | 5.5 | 2.54 |
| | 8.0 | 1.3 | 8.0 | 3.27 |
| streptavidin (STR) | 1 | 0.066 | 1 | 0.76 |
| | 2.5 | 1.2 | 2.5 | 1.6 |
| | 5.5 | 2.4 | 5.5 | 4.4 |
| | 8.0 | 3.0 | 8.0 | 5.6 |

-continued

| Protein | SSC | | Compound 2 | |
|---|---|---|---|---|
| | Dye:Protein Ratio | Degree of Substitution | Dye:Protein Ratio | Degree of Substitution |
| | 10 | 3.9 | 10 | 6.0 |
| | 20 | 4.9 | 20 | 6.0 |
| | 30 | 5.1 | 30 | 6.9 |

As shown above, the use of the reactive dye of the present invention as a labeling reagents results in a greater degree of dye incorporation into the protein at similar molar ratios of reactive dye to protein.

Example 20

Preparation of an Energy-transfer Conjugate

Conjugates of R-Phycoerythrin (R-PE) with Compound 2 (Example 2) or SSC are prepared as described in Example 19 at dye/protein ratios of 10, 20 and 30. The purified conjugates are then excited at 488 nm, and the emission spectra are recorded. The R-PE conjugate of Compound 2 (prepared with a dye/protein ratio of 20) exhibits significant energy transfer with little fluorescence emission at the wavelengths expected for the R-PE fluorophore, while the R-PE conjugate of SSC exhibits relatively poor energy transfer.

The R-PE conjugate of Compound 2 possesses significant utility as a second color probe used in conjunction with a first green or yellow-green emitting dye. Although the R-PE conjugate is successfully excited at the same wavelengths as typical green dyes, its emission is shifted to wavelengths appropriate for sulforhodamine 101.

Example 21

Hydrolytic Stability of Compound 2

Compound 2 and SSC are separately dissolved in solutions that are 90% DMF and 10% aqueous sodium bicarbonate. Each solution is analyzed using thin layer chromatography (TLC) as follows: An aliquot from each sample is diluted 1:100 in methanol and 1 µL of the resulting solution is spotted on a silica gel TLC plate and developed in 15% methanol in chloroform. The SSC reagent is so labile that it does not withstand the TLC conditions and decomposes immediately upon application to the TLC plate. However, only 10–20% of Compound 2 appears to decompose even after two hours of incubation in the presence of water.

Example 22

The Effect of Hydrolytic Stability on Protein Labeling Efficiency

Compound 2 and SSC are separately dissolved at room temperature in solutions that are 25% DMF and 75% aqueous sodium bicarbonate. After periods of 1, 5, 10, 20, 30, and 60 minutes, the dye solutions are used to label goat IgG protein at a dye/protein ratio of 10 and a protein concentration of 10 mg/mL in 100 mM sodium bicarbonate. The resulting protein conjugates are purified as described in Example 19. The resulting degrees of substitution are shown below:

| Time | Degree of Substitution | |
|---|---|---|
| (minutes) | SSC | Compound 2 |
| 1 | 0.30 | 4.09 |
| 5 | — | 3.64 |
| 10 | — | 3.38 |
| 20 | — | 2.96 |
| 30 | — | 3.00 |
| 60 | — | 2.78 |

Due to the high hydrolytic instability of SSC, no protein conjugate is formed when the reagent is exposed to water at room temperature for as little as five minutes. In contrast, the labeling of proteins using Compound 2 of the present invention results in adequate labeling even after 1 hour in aqueous solution.

Example 23

Figure 5:
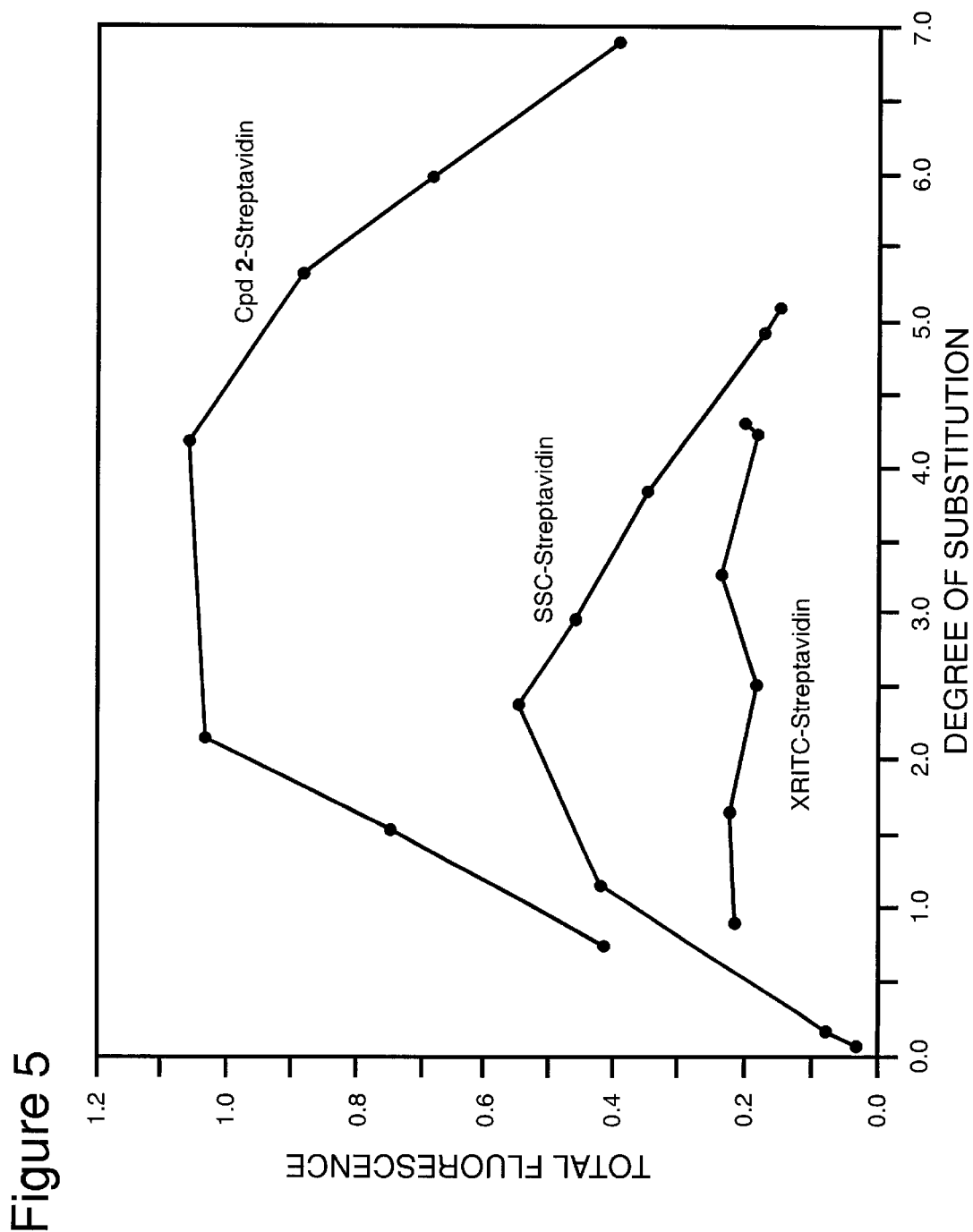
FIG. 5: A comparison of total fluorescence as a function of the degree of fluorophore substitution for streptavidin conjugates of XRITC, SSC and Compound 2 (Example 23).

Total Fluorescence of Selected Dye Conjugates as a Function of Degree of Substitution The total fluorescence of selected conjugates of the dyes of the present invention is plotted against the degree of substitution of the conjugate. Total fluorescence is the product of the degree of substitution and the quantum yield, relative to a common standard (in this case, sulforhodamine 101). The degree of substitution is determined as described earlier (Example 19). The results of this calculation for streptavidin conjugates of SSC, Compound 2, and XRITC show the optimal degree of substitution for each conjugate and the relative fluorescence intensity of conjugates made with each dye, as plotted graphically in FIG. 5. As shown, as the degree of substitution increases, the total fluorescence increases, until the point at which the quantum yield begins to decrease due to crowding of the dye molecules and the resultant fluorescence quenching, thereby canceling the effect of additional dye substitution.

Example 24

Utility of Protein Conjugates as Immunoreagents

The succinimidyl ester derivative Compound 2 is used to prepare conjugates of streptavidin that are further utilized in immunochemistry experiments. In particular, the efficacy of the streptavidin conjugate of Compound 2 (prepared as described in Example 19) is tested in parallel with the streptavidin conjugate of SSC. The comparison is performed using a test to detect antinuclear antibodies commercially available from INOVA Diagnostics Inc. (San Diego, Calif.). The commercial assay consists of a series of fixed cells on slides, and an autoimmune serum against cell nuclei. The two streptavidin conjugates of Compound 2 exhibit degrees of substitution of 2.2 and 4.2 moles of dye per mole of protein, respectively, while the two streptavidin conjugates of SSC exhibit degrees of substitution of 2.4 and 3.9 dyes per mole. The cell nuclei are treated with either positive serum or negative serum (as a control), and are then developed with biotinylated protein A. Each of the streptavidin conjugates above is then used to label the treated cells at a concentration of 5 µg/mL. Each of the Compound 2 streptavidin conjugates yield lower fluorescence background and brighter nuclear staining than the corresponding SSC-streptavidins (approximately two-fold more fluorescent, as measured using a fluorescent microscope coupled to a Photometrics Star-1 cooled CCD camera for quantitative digital imaging).

Example 25

Labeling Efficiency of Thiol-reactive Dyes

The thiol-reactive dyes Compound 5 (iodoacetamide-modified), Compound 6 (bromoacetamide-modified) and Compound 7 (maleimide-modified) are tested for labeling efficiency by reacting the dyes with b-galactosidase, an enzyme with more then 10 free thiol groups per molecule. Each dye is dissolved at a concentration of 10 mg/mL in DMF and added to 3 mg of the protein dissolved at 10 mg/mL in 0.1 M phosphate, 0.1 M NaCl pH 7.5. The dyes are added at molar ratios of 10 for the maleimide and 20 and 40 for both the bromoacetamide and the iodoacetamide, respectively. The reaction is continued for 1 hour at room temperature under argon, and the conjugates are purified using column chromatography. The degree of substitution obtained using each of the three compounds is shown below:

| | Reactive Dye: Protein Ratio | | |
|---|---|---|---|
| Reactive Dye | 10 | 20 | 40 |
| Compound 5 | — | 4.91 | 5.14 |
| Compound 6 | — | 4.20 | 4.70 |
| Compound 7 | 7.63 | — | — |

As demonstrated by the above data, the thiol-reactive dyes are useful for labeling proteins which have free thiol groups.

Example 26

Solubility of Compound 2

The solubility of Compound 3 is determined by dissolving the reactive dye in 0.1 M aqueous sodium bicarbonate, in the absence of organic solvents at room temperature. This sulfosuccinimidyl ester possesses a solubility of about 10 mg/mL, when dissolution is facilitated by the use of sonication.

Example 27

Preparation of a Dextran Conjugate of Sulforhodamine 101

The dichlorotriazine derivative (Compound 13) is used to label the hydroxyl groups of a polysaccharide with sulforhodamine 101 fluorophores. A 40,000 MW dextran (50 mg) is dissolved in 2.5 mL of 0.2 M sodium carbonate buffer (pH 9.5) and the resulting solution is heated to 50° C. in a temperature controlled bath. A solution of 20 mg of Compound 5 in 1 mL DMSO is added to the dextran solution with stirring. The reaction is continued for 6 hours, maintaining the pH at 9.5–10.0 by the addition of aliquots of 1 M NaOH. The dye-dextran conjugate is then purified on a SEPHADEX G-50 resin chromatographic column that has been equilibrated with 30 mM ammonium acetate. The first colored band to elute is collected, and the dextran solution is lyophilized. The degree of labeling is determined as in Example 19. The degree of substitution obtained is 5 dyes/40,000 daltons of dextran.

Example 28

Preparation of an Aminodextran Conjugate of Sulforhodamine 101

A sample of aminodextran (50 mg) having an average molecular weight of 70,000 and derivatized with an average of 13 amino groups, is dissolved in 0.1 M sodium bicarbonate to give a concentration of 10 mg/mL. A solution of Compound 2 in DMF having a concentration of 10 mg/mL is added to the dextran solution in an amount to give a dye/protein ratio of 12. After stirring at room temperature, the conjugated dextrans are purified by gel filtration using SEPHADEX G-50 resin in water. The dextran solution is lyophilized, and the degree of substitution of the dextran is determined as described in Example 19. The dextran-conjugate exhibits a DOS of 6 dyes/70,000 daltons of dextran.

Aminodextran having an average molecular weight of 40,000 and derivatized with 7 amino groups is conjugated exactly analogously, using a dye/protein ratio of 8. The resulting dextran-conjugate exhibits a DOS of 3 dyes/40,000 daltons of dextran.

Example 29

Labeling Actin in Cells Using a Phalloidin Conjugate of Sulforhodamine 101

Mammalian cells are grown on coverslips according to standard tissue culture procedures. After two days in culture, the growth medium is removed and the cells are rinsed twice with warm Hanks Balanced Salt Solution (HBSS; 0.14 g/L $CaCl_2$, 0.40 g/L KCl, 0.06 g/L $KH_2PO_4$, 0.10 g/L $MgCl_2.6H_2O$, 0.10 g/L $MgSO_4.7H_2O$, 8.0 g/L NaCl, 0.35 g/L $NaHCO_3$, 0.48 g/L $Na_2HPO_4$, 1 g/L D-glucose). Cells are then fixed in 3.7% formaldehyde diluted into HBSS for 10 minutes at room temperature. Cells are rinsed in phosphate buffered saline (PBS; 0.20 g/L KCl, 0.20 g/L $KH_2PO_4$, 8 g/l NaCl, 1.15 g/L $Na_2HPO_4$), and permeabilized in ice cold acetone for 10 minutes. The cells are then rehydrated in PBS for 10 minutes, and stained with a 165 nM solution of Compound 4 in PBS. The stained cells are then rinsed twice with PBS, mounted in the mounting medium of choice, and viewed using a standard filter set used for SSC conjugates on a fluorescence microscope. The staining of F-actin filaments using Compound 4 is consistent with that of similar, shorter wavelength phallotoxin conjugates.

Example 30

Labeling Actin in Cells Using a Phalloidin Conjugate of Sulforhodamine in Conjunction with a Labeled Antibody Cells are grown, fixed and permeabilized as described in Example 29. After a 10 minutes rehydration in PBS, cells are blocked in a solution of 1% bovine serum albumin/1% normal goat serum/0.1% TWEEN-20 in PBS for 30 minutes. Monoclonal anti-tubulin antibody is diluted into the blocking buffer at a concentration of 2 µg/mL (Boehringer Mannheim, Indianapolis, Ind.) and a 100 µL volume per coverslip is incubated with the cells for 1 hour. After rinsing in PBS, fluorescein goat anti-mouse antibody is diluted to 10 µg/mL and incubated with the cells for 30 minutes. After rinsing in PBS, cells are then incubated with a 165 nM solution of Compound 4 diluted in PBS for 30 minutes. Cells are rinsed a final time in PBS, mounted in the mounting medium of choice, and viewed through either a multiband filter, or through a long-wavelength filter and a fluorescein filter with a standard fluorescence microscope. Simultaneous staining of both F-actin and tubulin filaments is consistent with staining by the individual probes.

Alternatively, cells may be prepared according to other methods of fixation and permeabilization.

Example 31

Fluorescence of Labeled Nucleotides

Two fluorescent conjugates of deoxyuridine-5'-triphosphate are prepared as in Example 4, only using 5-(3-amino-1-propynyl)-2'-deoxyuridine-5'-triphosphate in place of 5-(3-aminoallyl)-2'-deoxyuridine-5'-triphosphate (as described in Hobbs, Jr. et al, supra). One conjugate is prepared using Compound 2, the other is prepared using SSC.

Figure 6:
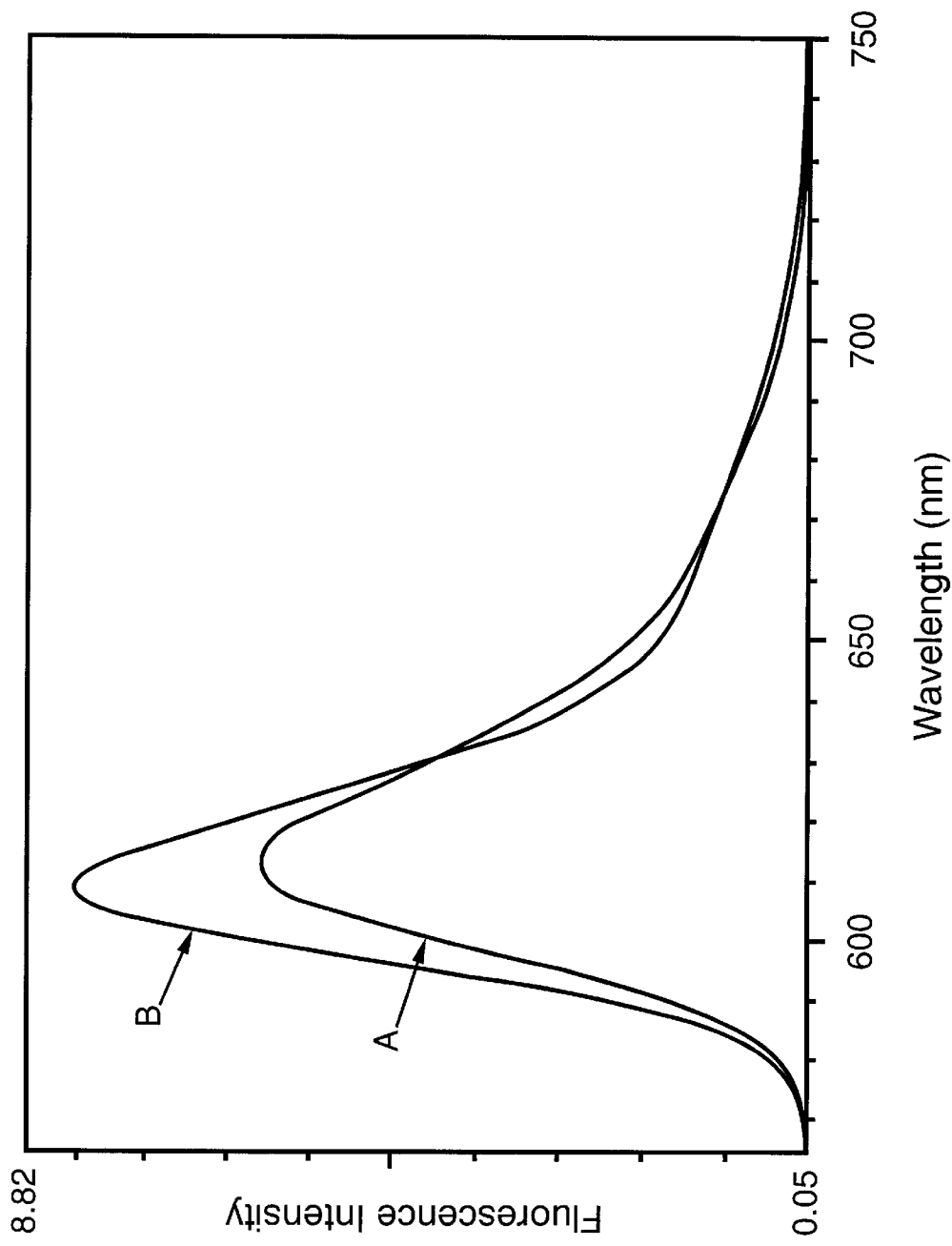
FIG. 6: A comparison of the fluorescence emission of conjugates of 2'-deoxyuridine-5'-triphosphate (Example 31). A) SSC-dUTP; B) Compound 2-dUTP.

The two conjugates are separately dissolved in pH 8 buffer, and the optical density of each solution is adjusted to 0.03 when measured at 560 nm. Each solution is then excited at 560 nm and the resulting fluorescence emission is recorded from 565 nm to 750 nm. The results are depicted in FIG. 6. The compound 2-dUTP conjugate exhibits a narrower emission spectrum than the SSC-dUTP conjugate. In addition, the SSC-dUTP conjugate displays a fluorescence yield that is only 75% of the measured fluorescence yield for the Compound 2-dUTP conjugate.

Example 32

Preparing a DNA Hybridization Probe Using Fluorescent Nucleotide Conjugates

For each labeling reaction, a microfuge tube containing about 1 µg of a ~700 bp Hind III—Bgl II fragment of the E. coli lacZ structural gene is heated for about 10 minutes at 95° C. to fully separate the strands. The DNA is immediately cooled on ice, to prevent the strands from reannealing. To the DNA mixture on ice is added 2 µL of a 2 mg/mL mixture of random sequence hexanucleotides, in 0.5 M Tris-HCl, pH 7.2, 0.1 M $MgCl_2$, 1 mM dithiothreitol; 2 µL of a dNTP labeling mixture (1 mM dATP, 1 mM dGTP, 1 mM dCTP, 0.65 mM dTTP and 0.35 mM either SSC labeled dUTP or Compound 2 labeled dUTP, as prepared in Example 4 or Example 31). Sterile distilled and deionized water is added to the samples to bring the total volume of each to 19 µL. A 1 µL volume of Klenow DNA polymerase (2 units/µL) is added carefully to the samples and they are mixed by pipetting up and down repeatedly. The samples are incubated for one hour at 37° C. The reactions are stopped by adding 2 µL of 0.2 M EDTA, pH 8.0. The labeled DNA is precipitated by addition of 2.5 µL of 4 M LiCl and 75 µL prechilled (−20° C.) 100% ethanol and mixing well. Precipitation is allowed to continue for 2 hours at −20° C. and the nucleic acids are then recovered by centrifugation at 5000 rpm in a microfuge. The pellets are washed briefly with cold 70% ethanol, then with cold 100% ethanol. The pellets are dried briefly and dissolved in 10 mM Tris-HCl, pH 8.0, 1 mM EDTA. A portion consisting of ⅒ to ½ of each sample is analyzed by gel electrophoresis on a 1% agarose minigel under standard conditions. Both the SSC labeled dUTP and the Compound 2 labeled dUTP give rise to clearly visible labeled DNA products that exhibit bright red fluorescence when visualized using ultraviolet trans or epi-illumination. The labeled DNA products are suitable for in situ hybridization experiments for the detection of RNA or DNA associated with the E. coli lacZ gene in cells or tissues.

It is to be understood that, while the foregoing invention has been described in detail by way of illustration and example, numerous modifications, substitutions, and alterations are possible without departing from the spirit and scope of the invention as described in the following claims.

What is claimed is:

1. A reactive dye having the formula

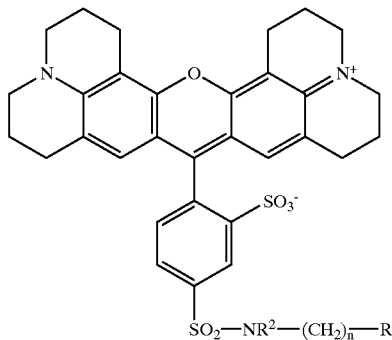

or the formula

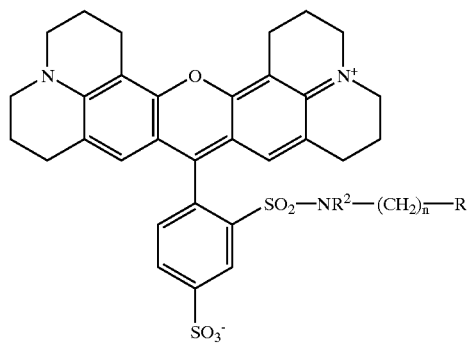

wherein
R$^2$ is H, C$_1$–C$_6$ alkyl or C$_1$–C$_6$ acyl; and
n=2 to 8; and
R is a halomethylbenzamidyl, maleimidyl, (3,5-dichloro-2,4,6-triazin-1-yl)amino, isocyanato or an isothiocyanato; or
n=1 to 7; and
R is a carboxylic acid, an alkali or alkaline earth metal salt of a carboxylic acid, or R is —(C=O)—R$_x$, where R$_x$ is a chloride, fluoride or azide; or R$_x$ is selected so as to make R a hydroxybenzotriazolyl ester, a succinimidyl ester, a sulfosuccinimidyl ester, an alkali or alkaline earth metal salt of a sulfosuccinimidyl ester, a symmetric anhydride that links two sulforhodamine 101 fluorophores, a mixed anhydride of a sulforhodamine 101 fluorophore and a chloroformate having 2–8 carbons, a mixed anhydride of a sulforhodamine 101 fluorophore and a carboxylic acid or perfluorinated carboxylic acid having 2–8 carbons, a mixed anhydride of a sulforhodamine 101 fluorophore and a sulfonic or fluorinated sulfonic acid having 1–8 carbons, or an ester of a phenol or a naphthol that is further substituted one or more times by nitro, sulfo, carboxy, alkali or alkaline earth metal salt of sulfo or carboxy, cyano, fluoro, chloro, or trifluoromethyl; or R$_x$ is selected so as to make R a carboxylic acid activated by a carbodiimide having 2–14 carbons.

2. A reactive dye, as claimed in claim 1, wherein n=2–8, and R is a halomethylbenzamido, maleimido, maleimidyl benzamido, maleimidyl alkylamido, azidobenzamido, azidoperfluorobenzamido, (3,5-dichloro-2,4,6-triazin-1-yl)amino, isocyanato or an isothiocyanato.

3. A reactive dye, as claimed in claim 2, wherein n=5 or 6.

4. A reactive dye, as claimed in claim 2, wherein R is maleimido or a halomethylbenzamido.

5. A reactive dye, as claimed in claim 2, wherein R is maleimido.

6. A reactive dye, as claimed in claim 5, having the formula

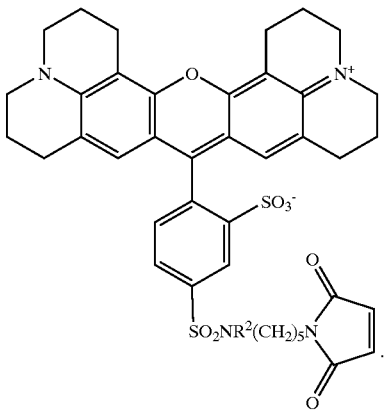

7. A reactive dye, as claimed in claim 1, wherein n=1–7 and R is a carboxylic acid, an alkali or alkaline earth metal salt of a carboxylic acid, or R is —(C=O)—R$_x$, where R$_x$ is a chloride, fluoride or azide; or R$_x$ is selected so as to make R a hydroxybenzotriazolyl ester, a succinimidyl ester, a sulfosuccinimidyl ester, an alkali or alkaline earth metal salt of a sulfosuccinimidyl ester, a symmetric anhydride that links two sulforhodamine 101 fluorophores, a mixed anhydride of a sulforhodamine 101 fluorophore and a chloroformate having 2–8 carbons, a mixed anhydride of a sulforhodamine 101 fluorophore and a carboxylic acid or perfluorinated carboxylic acid having 2–8 carbons, a mixed anhydride of a sulforhodamine 101 fluorophore and a sulfonic or fluorinated sulfonic acid having 1–8 carbons, or an ester of a phenol or a naphthol that is further substituted one or more times by nitro, sulfo, carboxy, alkali or alkaline earth metal salt of sulfo or carboxy, cyano, fluoro, chloro, or trifluoromethyl; or R$_x$ is selected so as to make R a carboxylic acid activated by a carbodiimide having 2–14 carbons.

8. A reactive dye, as claimed in claim 7, wherein R$_x$ is selected so as to make R an ester of a phenol or a naphthol that is further substituted one or more times by nitro, sulfo, carboxy, alkali or alkaline earth metal salt of sulfo or carboxy, cyano, fluoro, chloro, or trifluoromethyl.

9. A reactive dye, as claimed in claim 7, wherein R has the formula —(C=O)—R$_x$, wherein R$_x$ is chloride, fluoride, or azide; or R$_x$ is selected so as to make R a succinimidyl ester, sulfosuccinimidyl ester, or an alkali or alkaline earth metal salt of sulfosuccinimidyl ester.

10. A reactive dye, as claimed in claim 7, wherein R$_x$ is selected so as to make R a succinimidyl ester, sulfosuccinimidyl ester, or an alkali or alkaline earth metal salt of sulfosuccinimidyl ester.

11. A reactive dye, as claimed in claim 10, wherein n=4 or 5.

12. A reactive dye, as claimed in claim 10, wherein R$_x$ is selected so as to make R a succinimidyl ester.

13. A reactive dye, as claimed in claim 12, having the formula

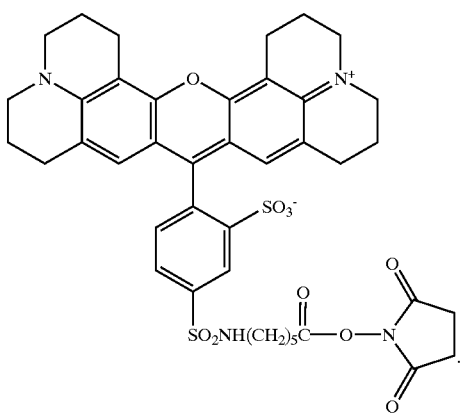

14. A kit for the fluorescent labeling of an organic substance, where said substance has at least one functional group that is an amine, a thiol, an alcohol, a phenol, an aldehyde, a ketone, a phosphate, an imidazole, a hydrazine, a hydroxylamine, a disubstituted amine, a trisubstituted amine, a halide, an epoxide, a sulfonate ester, or a carboxylic acid; comprising:

a) a reactive dye of the formula

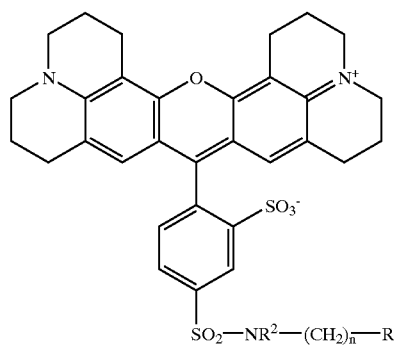

or the formula

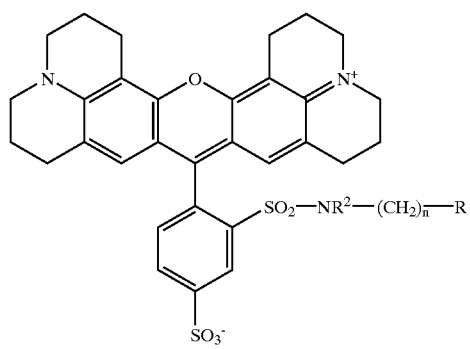

wherein

R2 is H, C1–C6 alkyl or C1–C6 acyl; and n=2 to 8; and

R is a halomethylbenzamidyl, maleimidyl, (3,5-dichloro-2,4,6-triazin-1-yl)amino, isocyanato or an isothiocyanato; or n=1 to 7; and R is a carboxylic acid, an alkali or alkaline earth metal salt of a carboxylic acid, or R is —(C=O)—$R_x$, where $R_x$ is a chloride, fluoride or azide; or $R_x$ is selected so as to make R a hydroxybenzotriazolyl ester, a succinimidyl ester, a sulfosuccinimidyl ester, an alkali or alkaline earth metal salt of a sulfosuccinimidyl ester, a symmetric anhydride that links two sulforhodamine 101 fluorophores, a mixed anhydride of a sulforhodamine 101 fluorophore and a chloroformate having 2–8 carbons, a mixed anhydride of a sulforhodamine 101 fluorophore and a carboxylic acid or perfluorinated carboxylic acid having 2–8 carbons, a mixed anhydride of a sulforhodamine 101 fluorophore and a sulfonic or fluorinated sulfonic acid having 1–8 carbons, or an ester of a phenol or a naphthol that is further substituted one or more times by nitro, sulfo, carboxy, alkali or alkaline earth metal salt of sulfo or carboxy, cyano, fluoro, chloro, or trifluoromethyl; or $R_x$ is selected so as to make R a carboxylic acid activated by a carbodiimide having 2–14 carbons;

such that R will spontaneously react with said functional group to yield a labeled substance; and b) instructions for combining the reactive dye with the substance and recovering the labeled substance.

15. A kit, as claimed in claim 14, wherein said substance is an amino acid, an amino acid polymer, a nucleotide, an oligonucleotide, an antisense oligonucleotide, a nucleic acid polymer, or a carbohydrate.

16. A kit, as claimed in claim 14, wherein said substance is an amino acid polymer.

17. A kit, as claimed in claim 14, wherein said substance is an oligonucleotide or nucleic acid polymer.

18. A kit, as claimed in claim 14, wherein said substance is a carbohydrate.

19. A kit, as claimed in claim 14, wherein said functional group is an amine or a thiol.

\* \* \* \* \*